(12) United States Patent
Goodman et al.

(10) Patent No.: US 9,200,054 B2
(45) Date of Patent: *Dec. 1, 2015

(54) SOMATOSTATIN ANALOGS WITH INHIBITORY ACTIVITY TO GROWTH HORMONE RELEASE

(71) Applicant: The Regents of the University of California, Oakland, CA (US)

(72) Inventors: Murray Goodman, La Jolla, CA (US); Sandra Blaj Moore, London (GB)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/030,970

(22) Filed: Sep. 18, 2013

(65) Prior Publication Data

US 2014/0179598 A1    Jun. 26, 2014

Related U.S. Application Data

(60) Continuation of application No. 13/077,659, filed on Mar. 31, 2011, now Pat. No. 8,562,948, which is a division of application No. 10/568,112, filed as application No. PCT/US2004/027128 on Aug. 20, 2004, now Pat. No. 7,968,080.

(60) Provisional application No. 60/496,942, filed on Aug. 20, 2003.

(51) Int. Cl.
| | | |
|---|---|---|
| *A61K 51/00* | (2006.01) | |
| *A61M 36/14* | (2006.01) | |
| *C07K 14/655* | (2006.01) | |
| *A61K 51/08* | (2006.01) | |

(52) U.S. Cl.
CPC ............. *C07K 14/6555* (2013.01); *A61K 51/08* (2013.01); *A61K 51/083* (2013.01)

(58) Field of Classification Search
CPC ..... A61K 51/00; A61K 51/08; A61K 51/083; A61K 51/088; C07K 14/6555
USPC ............. 424/1.11, 1.65, 1.69, 9.1, 9.2; 514/1, 514/1.1, 6.9, 13.3, 16.6, 16.7, 19.3, 21.1, 514/11.1, 11.2, 11.3, 11.4, 11.8, 19.2, 19.4, 514/19.5, 19.6, 19.7, 21.7; 530/300, 311, 530/317, 328, 329, 400
See application file for complete search history.

(56) References Cited

U.S. PATENT DOCUMENTS

| | | | |
|---|---|---|---|
| 3,842,067 A | 10/1974 | Sarantakis | |
| 3,862,925 A | 1/1975 | Sarantakis | |
| 3,904,594 A | 9/1975 | Guillemin | |
| 3,972,859 A | 8/1976 | Fujino | |
| 4,816,438 A | 3/1989 | Spiess | |
| 5,436,155 A | 7/1995 | Bell | |
| 5,620,675 A | 4/1997 | McBride | |
| 5,668,006 A | 9/1997 | Hadcock | |
| 5,716,596 A | 2/1998 | Dean | |
| 5,929,209 A | 7/1999 | Hadcock | |
| 6,001,801 A | 12/1999 | Coy | |
| 6,159,443 A | 12/2000 | Hallahan | |
| 6,602,849 B1 | 8/2003 | Gordon | |
| 7,968,080 B2 * | 6/2011 | Goodman et al. | ............ 424/1.69 |
| 8,562,948 B2 * | 10/2013 | Goodman et al. | ............ 424/1.69 |

FOREIGN PATENT DOCUMENTS

| | | |
|---|---|---|
| GB | 8927255.3 | 6/1990 |
| WO | 93/18797 A1 | 9/1993 |

OTHER PUBLICATIONS

Bakker et al., "In Vivo Use of a Radioiodinated Somatostatin Analogue: Dynamics, Metabolism, and Binding to Somatostatin Receptor-Positive Tumors in Man," J. Nucl. Med. 32:1184-1189 (1991).
Bussey et al., "The nucleotide sequence of chromosome I from Saccharomyces cerevisiae," Proc. Natl. Acad. Sci., 92:3809-3813 (1995).
Pradayrol et al., "N-terminaly Extended Somatostatin: The Primary Structure of Somatostatin-28," FEBS Letters, 109:55-58 (1980).
Raynor et al., "Clones Somatostatin Receptors: Identification of Subtype-Selective Peptides and Demonstration of High Affinity Binding of Linear Peptides," Mol. Pharm., 43:838-844 (1993).
Smith-Jones et al., "DOTA-Lanreotide: A Novel Somatostatin Analog for Tumor Diagnosis and Therapy," Endocrinology, 140:5136-5148 (1999).
Woltering et al., "Detection of occult gastrinomas with iodine 125-labeled lanreotide and intraoperative gamma detection," Surgery, 116:1139-1147 (1994).
Golub et al., Science, Oct. 15, 1999, pp. 531-537.

* cited by examiner

*Primary Examiner* — D L Jones
(74) *Attorney, Agent, or Firm* — Gavrilovich, Dodd & Lindsey LLP; Joseph R. Baker, Jr.

(57) ABSTRACT

Provided are therapeutic and diagnostic somatostatin analogs including radiotherapeutic and radiodiagnostic reagents, and methods of making and use thereof.

16 Claims, No Drawings

US 9,200,054 B2

SOMATOSTATIN ANALOGS WITH INHIBITORY ACTIVITY TO GROWTH HORMONE RELEASE

CROSS REFERENCE TO RELATED APPLICATION

This application is a continuation of U.S. patent application Ser. No. 13/077,659, filed Mar. 31, 2011, which is a divisional and claims priority to U.S. patent application Ser. No. 10/568,112, filed Sep. 27, 2006, which is a U.S. National Stage application filed under 35 U.S.C. 371 and claims priority to PCT/US04/27128, filed Aug. 20, 2004, which claims priority under 35 U.S.C. §119 to provisional application Ser. No. 60/496,942, filed Aug. 20, 2003, the disclosures of which are incorporated herein by reference.

STATEMENT REGARDING FEDERALLY SPONSORED RESEARCH

This invention was made with Government support of Grant No. DK 15410, awarded by the National Institutes of Health. The Government has certain rights in this invention.

TECHNICAL FIELD

This invention relates to somatostatin analogs and more particularly to somatostatin analogs that specifically interact with certain somatostatin receptor subtypes.

BACKGROUND

Somatostatin (SS) is an endogenous peptide that acts as a hormone, neurotransmitter and neuromodulator, as well as a paracrine regulator of neighboring cells. It is present in two forms, SS-14 and SS-28, a tetradecapeptide and a 28 amino acid peptide, which originate in the protein preprosomatostatin and are distributed differently in neuroendocrine and central and peripheral nervous system tissues. There are five subtypes of somatostatin receptors, all G protein-coupled receptors with a high sequence homology.

Despite the commercial availability of octreotide, lanreotide, and vapreotide, a large number of somatostatin analogs have been proposed for use as imaging and/or therapeutic agents to detect and/or treat cancer and other somatostatin-responsive disease states. Analogs with higher affinity to somatostatin receptors (SSTs) and to SST subtypes, in particular to SST2 and SST5 are desirable, such that lower dosages of somatostatin analogs may be administered to obtain a clinical response.

SUMMARY

The invention provides cyclic peptidomimetic somatostatin analogs, which are designed to satisfy the need for potent and selective SST2 and SST5 ligands. The presence of the functionalized aromatic amino acids opens the way to new "handles" for additional functionalization and broader applications.

The analogs of the invention are beneficial anti-tumor agents. They may be used for the treatment of acromegaly and diabetes, as well as for scintigraphy purposes when radioactively labeled. In addition, the analogs may be radioactively labeled and/or linked to cytotoxic agents capable of causing cell death (e.g., tumor cell death).

The compositions (i.e., the SS analogs) of the invention are useful as ligands that are designed to interact with certain SST subtypes (e.g., SST2 and SST5) on cells in vitro and in vivo.

The invention provides a somatostatin (SS) analog, wherein the analog is selected from any one of 4-amino-D-Phe-c[Cys-Tyr-D-Trp-Lys-Val-Cys]-Asp-$NH_2$; 4-amino-D-Phe-c[Cys-Tyr-D-Trp-Lys-Val-Cys]-Thr-$NH_2$; 4-amino-D-Phe-c[Cys-Tyr-D-Trp-Lys-Val-Cys]-D-Asp-$NH_2$; 4-amino-D-Phe-c[Cys-Tyr-D-Trp-Lys-Val-Cys]-D-Thr-$NH_2$; 4-amino-D-Phe-c[Cys-(3-iodo)-Tyr-D-Trp-Lys-Val-Cys]-Thr-$NH_2$; 4-amino-3-iodo-D-Phe-c[Cys-Tyr-D-Trp-Lys-Val-Cys]-Thr-$NH_2$; 4-amino-3-iodo-D-Phe-c[Cys-Tyr-D-Trp-Lys-Val-Cys]-Asp-$NH_2$; 4-amino-3-iodo-D-Phe-c[Cys-(3-iodo)-Tyr-D-Trp-Lys-Val-Cys]-Thr-$NH_2$; 4-amino-3-iodo-D-Phe-c[Cys-(3-iodo)-Tyr-D-Trp-Lys-Val-Cys]-Asp-$NH_2$; and D-Phe-C[Cys-Tyr-D-Trp-Lys-Val-Cys]-Asp-$NH_2$. In one aspect of the invention, the SS analog can be linked to a radioactive element.

The invention further provides methods of visualizing malignant cells in a subject comprising administering to the subject an SS analog of the invention.

Also provided by the invention is a method of treating various proliferative disorders in a subject comprising administering to the subject an SS analog of the invention. In one aspect of the invention the proliferative disorder comprises a tumor, acromegaly, and/or diabetes.

The invention also provides somatostatin (SS) analogs that are designed to bind selectively to SS receptor 2 (SST2) and/or SST5 in contrast to other SS receptors, wherein the SS analog has a structure selected from the group consisting of 4-amino-D-Phe-c[Cys-Tyr-D-Trp-Lys-Val-Cys]-Asp-$NH_2$; 4-amino-D-Phe-c[Cys-Tyr-D-Trp-Lys-Val-Cys]-Thr-$NH_2$; 4-amino-D-Phe-c[Cys-Tyr-D-Trp-Lys-Val-Cys]-D-Asp-$NH_2$; 4-amino-D-Phe-c[Cys-Tyr-D-Trp-Lys-Val-Cys]-D-Thr-$NH_2$; 4-amino-D-Phe-c[Cys-(3-iodo)-Tyr-D-Trp-Lys-Val-Cys]-Thr-$NH_2$; 4-amino-3-iodo-D-Phe-c[Cys-Tyr-D-Trp-Lys-Val-Cys]-Thr-$NH_2$; 4-amino-3-iodo-D-Phe-c[Cys-Tyr-D-Trp-Lys-Val-Cys]-Asp-$NH_2$; 4-amino-3-iodo-D-Phe-c[Cys-(3-iodo)-Tyr-D-Trp-Lys-Val-Cys]-Thr-$NH_2$; 4-amino-3-iodo-D-Phe-c[Cys-(3-iodo)-Tyr-D-Trp-Lys-Val-Cys]-Asp-$NH_2$; and D-Phe-C[Cys-Tyr-D-Trp-Lys-Val-Cys]-Asp-$NH_2$ and compounds containing di- or polyiodinated aromatic residues.

The invention also provides a pharmaceutical composition comprising a mixture of an SS analog of the invention and at least one pharmaceutically acceptable carrier.

The details of one or more embodiments of the invention are set forth in the description below. Other features, objects, and advantages of the invention will be apparent from the description and from the claims.

DETAILED DESCRIPTION

Somatostatin inhibits the release of insulin and glucagon from the pancreas, inhibits growth hormone release from the pituitary and reduces gastric secretions. The half-life in plasma of native somatostatin is less than 3 minutes. It is rapidly degraded by peptidases. As a consequence, somatostatin analogs with improved bioavailability, as well as receptor specificity, are currently being sought. Somatostatin and its analogs are likely to be involved with treatment of various diseases. The number and variety of diagnostic and therapeutic uses for SS analogs, especially for receptor-specific peptidomimetic and non-peptidic receptor-specific ligands have proliferated.

Numerous tissues in the human body express somatostatin receptors including, but not limited to: (1) the gastrointestinal tract, (2) the peripheral nervous system, (3) the endocrine system, (4) the vascular system, and (5) lymphoid tissue, where the receptors are located in germinal centers. In all these cases, somatostatin binding is of high affinity and specific for bioactive somatostatin analogs. After binding of ligands to somatostatin receptors, the agonist-receptor complexes are internalized by cells. This property is important practically, and constitutes the basis of localization and treatment of tumors which over-express somatostatin receptors.

Somatostatin receptors are also expressed in pathological states, particularly in neuroendocrine tumors of the gastrointestinal tract. Most human tumors originating from the somatostatin target tissue have conserved their somatostatin receptors. It was first observed in growth hormone-producing adenomas and TSH-producing adenomas; about one-half of endocrine inactive adenomas display somatostatin receptors. Ninety percent of the carcinoids and a majority of islet-cell carcinomas, including their metastasis, usually have a high density of somatostatin receptors. However, only 10 percent of colorectal carcinomas and none of the exocrine pancreatic carcinomas contain somatostatin receptors. The somatostatin receptors in tumors can be identified using in vitro binding methods or using in vivo imaging techniques; the latter allow the precise localization of the tumors and their metastases in subjects. Because somatostatin receptors in gastroenteropancreatic tumors are functional, their identification can be used to assess the therapeutic efficacy of an analog to inhibit excessive hormone release subjects.

The cyclic tetradecapeptide somatostatin-14 (SS-14) was originally isolated from the hypothalamus and characterized as an inhibitor of growth hormone release from the anterior pituitary (see, e.g., U.S. Pat. No. 3,904,594, incorporated herein by reference). This tetradecapeptide has a bridging or cyclizing bond between the sulfhydryl groups of the two cysteinyl amino acid residues in the 3 and 14 positions. SS-14 regulates insulin, glucagon, and amylase secretion from the pancreas, and gastric acid release in the stomach. For example, SS-14 inhibits the effects of pentagastrin and histamine on the gastric mucosa. SS-14 is also expressed in intrahypothalamic regions of the brain and has a role in the regulation of locomotor activity and cognitive functions. SS-14 is present throughout the central nervous system and acts as a neurotransmitter. In the central nervous system, SS-14 has been shown to both positively and negatively regulate neuronal firing, to affect the release of other neurotransmitters, and to modulate motor activity and cognitive processes.

SS-14 affects multiple cellular processes. Studies have shown that SS-14 is an inhibitory regulator of adenylyl cyclase in different tissues. SS-14 also regulates the conductance of ionic channels, including both potassium and calcium channels. These actions of SS-14 are mediated via pertussis toxin-sensitive guanine nucleotide-binding proteins. SS-14 also regulates the activity of tyrosine phosphatases and cellular proliferation through pertussis toxin-insensitive mechanisms.

SS-14 induces its biological effects by interacting with a family of membrane-bound structurally similar receptors. Five SS-14 receptors have been cloned and are referred to as SST 1-5. Human SST1, mouse SST2 and mouse SST3 are described in Raynor et al., Molecular Pharmacology, 43, 838-844 (1993), and all five human SS receptors are now available for research purposes. Human SST1, 2 and 3 are also disclosed in U.S. Pat. No. 5,436,155. Additional SS-14 receptors are disclosed in U.S. Pat. Nos. 5,668,006 and 5,929,209. All five receptors bind SS-14 and SS-28 with high affinity. Selective agonists of SST2 and SST5 have been identified and used to reveal distinct functions of these receptors. These two receptors are believed to be the predominant subtypes in peripheral tissues. SST2 is believed to mediate the inhibition of growth hormone, glucagon and gastric acid secretion. In contrast, SST5 appears to be primarily involved in the control of insulin and amylase release. SST3 is found in cortex tissue, in the pituitary and in adenoma tumor tissue; it is believed to mediate inhibition of gastric smooth muscle contraction upon binding by SS-14. These findings indicate that different receptor subtypes mediate distinct functions of SS-14 in the body.

Somatostatin binds to five distinct receptor (SSTs) subtypes with relatively high affinity for each subtype. Binding of agonists to the different SST subtypes have been associated with the treatment of the following conditions and/or diseases. Activation of types 2 and 5 have been associated with growth hormone suppression and more particularly GH secreting adenomas (Acromegaly) and TSH secreting adenomas. Activation of type 2 but not type 5 has been associated with treating prolactin-secreting adenomas. Other indications associated with activation of the somatostatin subtypes are restenosis, inhibition of insulin and/or glucagon and more particularly diabetes mellitus, hyperlipidemia, insulin insensitivity, Syndrome X, angiopathy, proliferative retinopathy, dawn phenomenon and Nephropathy; inhibition of gastric acid secretion and more particularly peptic ulcers, enterocutaneous and pancreaticocutanieous fistula, irritable bowel syndrome, Dumping syndrome, watery diarrhea syndrome, AIDS-related diarrhea, chemotherapy-induced diarrhea, acute or chronic pancreatitis and gastrointestinal hormone secreting tumors; treatment of cancer such as hepatoma; inhibition of angiogenesis, treatment of inflammatory disorders such as arthritis; chronic allograft rejection; angioplasty; preventing graft vessel and gastrointestinal bleeding. Somatostatin agonists can also be used for decreasing body weight in a patient.

Somatostatin-28 (SS-28) was isolated from porcine upper small intestine (L. Pradayrol, et al. in FEBS Letters 109:55-58, 1980). SS-28 is an N-terminally extended version of SS-14 that has an additional 14 amino acid residues and which shows some increased potency when administered in vivo.

A cyclic SS-14 analog, termed SMS-201-995 (Octreotide), i.e. D-Phe-c[Cys-Phe-D-Trp-Lys-Thr-Cys]-Thr-ol is being used clinically to inhibit certain tumor growth. This analog has been shown to improve quality of life for the treated subject and there is strong evidence for control of tumor growth and reduction in mortality. Two similar octapeptide analogs, i.e. Lanreotide (D-β-Nal-c[Cys-Tyr-D-Trp-Lys-Val-Cys]-Thr-NH$_2$) and Vapreotide (D-Phe-c[Cys-Tyr-D-Trp-Lys-Val-Cys]-Trp-NH$_2$), have also been developed, see Smith-Jones et al., Endocrinology, 140, 5136-5148 (1999). These somatostatin analogs have been developed for use in radioimaging or as radiopharmaceuticals in radionuclide therapy. For radioimaging labeling with $^{123}$I can be used as disclosed in U.K. Patent Application 8927255.3 and as described in Bakker et al., J. Nucl. Med., 32:1184-1189, 1991. Typically proteins have been radiolabeled through the use of chelating agents, and there are various examples of complexing somatostatin analogs with $^{99}$Tc, $^{90}$Y or $^{111}$In, see U.S. Pat. Nos. 5,620,675 and 5,716,596. For example Octreotide scintigraphy is based on the visualization of octreotide-binding receptor(s). For these purposes, a radiolabeled form of octreotide, such as [$^{123}$I-Tyr]-octreotide was used. This and other developed analogs (Lanreotide (D-Nal-c[Cys-Tyr-D-Trp-Lys-Val-Cys]-Thr-NH$_2$; Vapreotide ((D-Phe-c[Cys-Tyr-D-Trp-Lys-Val-Cys]-Trp-NH$_2$); AN-238, which is RC-121 (D-Phe-c[Cys-Tyr-D-Trp-Lys-Val-Cys]-

Thr-NH$_2$) linked to a cytotoxic agent), are part of the arsenal presently available in the anti-cancer arena.

Somatostatin agonists have also been disclosed to be useful for inhibiting the proliferation of *Helicobacter pylori*.

Octreotide and other clinically used SS-14 analogs interact significantly with three of the receptor subtypes, i.e. SST2, SST3 and SST5. SST2 and SST5 have been reported to mediate antiproliferative effects of SS-14 on tumor cell growth; therefore, they may mediate the clinical effects of Octreotide in humans. For example, compound RC-121 is less potent than natural SS-14 and sandostatin, but presents the advantage of binding selectively to receptors SST2 and SST5 (see, e.g., Table 1).

TABLE 1

Binding Affinities of SS-14, Sandostatin, and RC-121

| Peptide | K$_i$(nM) ± SEM | | | | |
|---|---|---|---|---|---|
| | SST1 | SST2 | SST3 | SST4 | SST5 |
| SS-14 | 2.3 ± 0.47 | 0.23 ± 0.04 | 1.17 ± 0.23 | 1.7 ± 0.3 | 1.4 ± 0.3 |
| Sandostatin | 875 ± 180 | 0.57 ± 0.08 | 26.8 ± 7.7 | >1000 | 6.8 ± 1.0 |
| RC-121 | >1000 | 1.7 ± 0.5 | >1000 | >1000 | 13.1 ± 1.2 |

The invention provides methods and compositions that selectively interact with SST2 and/or SST5. It is believed that the inhibition of growth hormone release is mediated through interaction of ligands with the SST2 receptor, or that both SST2 and SST5 are implicated. It is also believed that interaction with SST5 is responsible for the insulin release inhibitory activity. Thus, analogs that are selective to either or both of these receptors would be useful for the treatment of cancer and diabetes among other uses.

The invention provides SS analogs having a modified terminal residue(s) with acidic and basic residues and/or peptidomimetic building blocks to improve potency, selectivity and bioavailability. The SS-14 analogs of the invention were developed based upon the parent compound (RC-121 D-Phe-c[Cys-Tyr-D-Trp-Lys-Val-Cys]-Thr-NH$_2$ because of the binding profile of this parent compound. The parent compound is selective for SST2 and SST5 (see, e.g., Table 1), but its properties can be improved from the standpoint of potency, stability in the biodomain and ratio of potencies at SST2 and SST5.

The SS-14 analogs of the invention provide several attractive features including (1) the analogs are readily synthesized from commercially available building blocks; (2) peptidomimetic modifications, designed to increase bioavailability (e.g., p-amino-D-phenylalanine, (2-amino-3-(4-aminophenyl)-propanoic acid) and 3-iodo-tyrosine, (2-amino-3-(4-hydroxy-3-iodophenyl)-propanoic acid)); (3) potent and selective-compound (4-amino-3-iodo)-D-Phe-c[Cys-Tyr-D-Trp-Lys-Val-Cys]-Thr-NH$_2$, which is designed to inhibit growth hormone in vitro more effectively than octreotide, used as a reference compound herein; and (4) the analogs are based, in part, on iodoaryl derivatives, such that radioactive labeling of these compounds is readily achieved using radioactive iodine. Such molecules are likely to have applications in visualization and eradication of malignant cells.

The invention provides SS-14 analogs comprising disulfide-bridged octapeptides incorporating non-natural amino acid building blocks. The invention provides SS-14 analogs of general formula I: X-c[Cys-Tyr-D-Trp-Lys-Val-Cys]-Y-NH$_2$, wherein X is selected from the group consisting of D-Phe, (4-amino)-D-Phe, and (4-amino-3-iodo)-D-Phe, wherein Y is selected from the group consisting of L- or D-Thr and L- or D-Asp, and wherein the Tyr at position 3 can be mono- or polyiodinated. Exemplary peptide structures according to formula I are provided in Table 2.

TABLE 2

| No. | Compound |
|---|---|
| 1 | D-Phe-c[Cys-Tyr-D-Trp-Lys-Val-Cys]-Asp-NH$_2$ |
| 2 | (4-amino)-D-Phe-c[Cys-Tyr-D-Trp-Lys-Val-Cys]-Thr-NH$_2$ |
| 3 | (4-amino)-D-Phe-c[Cys-Tyr-D-Trp-Lys-Val-Cys]-Asp-NH$_2$ |
| 4 | (4-amino)-D-Phe-c[Cys-Tyr-D-Trp-Lys-Val-Cys]-D-Thr-NH$_2$ |
| 5 | (4-amino)-D-Phe-c[Cys-Tyr-D-Trp-Lys-Val-Cys]-D-Asp-NH$_2$ |

TABLE 2-continued

| No. | Compound |
|---|---|
| 6 | (4-amino)-D-Phe-c[Cys-(3-iodo)-Tyr-D-Trp-Lys-Val-Cys]-Thr-NH$_2$ |
| 7 | (4-amino-3-iodo)-D-Phe-c[Cys-Tyr-D-Trp-Lys-Val-Cys]-Thr-NH$_2$ |
| 8 | (4-amino-3-iodo)-D-Phe-c[Cys-Tyr-D-Trp-Lys-Val-Cys]-Asp-NH$_2$ |
| 9 | (4-amino-3-iodo)-D-Phe-c[Cys-(3-iodo)-Tyr-D-Trp-Lys-Val-Cys]-Thr-NH$_2$ |
| 10 | (4-amino-3-iodo)-D-Phe-c[Cys-(3-iodo)-Tyr-D-Trp-Lys-Val-Cys]-Asp-NH$_2$ |

The nomenclature used to define the peptides is as described in M Goodman, A Felix, L Moroder and C Toniolo (Eds.). Synthesis of Peptides and Peptidomimetics, (2003) wherein, in accordance with conventional representation, the amino group appears to the left and the carboxyl group to the right. The standard 3-letter abbreviations to identify the alpha-amino acid residues, and where the amino acid residue has isomeric forms, it is the L-form of the amino acid that is represented unless otherwise expressly indicated, e.g. Ser=L-serine. By D, L is meant a mixture of the D- and L-isomers of a particular α-amino acid.

In another aspect, the invention provides a pharmaceutical composition comprising an effective amount of a compound of formula (I) or a pharmaceutically acceptable salt thereof and a pharmaceutically acceptable carrier.

In still another aspect, the invention provides a method of eliciting a somatostatin receptor agonist effect in a subject in need thereof, which comprises administering to said mammal an effective amount of a compound of formula (I) or a pharmaceutically acceptable salt thereof.

In another aspect, the invention provides a method of treating prolactin-secreting adenomas, restenosis, diabetes mellitus, hyperlipidemia, insulin insensitivity, Syndrome X, angiopathy, proliferative retinopathy, dawn phenomenon, Nephropathy, gastric acid secretion, peptic ulcers, enterocutaneous and pancreaticocutaneous fistula, irritable bowel syndrome, Dumping syndrome, watery diarrhea syndrome, AIDS-related diarrhea, chemotherapy-induced diarrhea, acute or chronic pancreatitis, gastrointestinal hormone secreting tumors, cancer, hepatoma, angiogenesis, inflammatory disorders, arthritis, chronic allograft rejection, angioplasty, graft vessel bleeding or gastrointestinal bleeding, in a subject in need thereof, which comprises administering to the subject a compound of formula (I) or a pharmaceutically acceptable salt thereof.

In another aspect, this invention provides a method of inhibiting the proliferation of *Helicobacter pylori* in a subject in need thereof, which comprises administering to the subject a compound of formula (I) or a pharmaceutically acceptable salt thereof.

A therapeutically effective amount of a peptide of the invention and a pharmaceutically acceptable carrier substance together form a therapeutic composition (e.g., a pill, tablet, capsule, or liquid) for administration (e.g., orally, intravenously, intravitreally, transdermally, pulmonarily, vaginally, subcutaneously, nasally, iontophoretically, or by intratracheally) to a subject in need of the peptide. The pill, tablet, or capsule can be coated with a substance capable of protecting the composition from the gastric acid or intestinal enzymes in the subject's stomach for a period of time sufficient to allow the composition to pass undigested into the subject's small intestine. The therapeutic composition can also be in the form of a biodegradable or nonbiodegradable sustained release formulation for subcutaneous or intramuscular administration. Continuous administration can also be obtained using an implantable or external pump to administer the therapeutic composition.

The dose of a peptide or therapeutic composition of the invention for treating the above-mentioned diseases or disorders varies depending upon the manner of administration, the age and the body weight of the subject, and the condition of the subject to be treated, and ultimately will be decided by the attending physician or veterinarian. Such an amount of the peptide or therapeutic composition as determined by the attending physician or veterinarian is referred to herein as a "therapeutically effective amount."

Selectivity for binding of the analog peptides of the invention to SST2 and/or SST5 can be demonstrated by testing their interaction with the five different cloned human SS-14 receptors. In vitro assays for the ability of analogs to bind to various somatostatin receptor subtypes are described herein and are known in the art (see, e.g., U.S. Pat. Nos. 6,602,849; and 6,001,801, the disclosures of which are incorporated herein by reference). Generally, recombinant cells expressing the receptor are washed and homogenized to prepare a crude protein homogenate in a suitable buffer, as known in the art. In a typical assay, an amount of protein from the cell homogenate is placed into a small volume of an appropriate assay buffer at an appropriate pH. Candidate substances, such as the analogs of the invention, are added to the admixture in convenient concentrations, and the interaction between the candidate substance (e.g., the analogs of the invention) and the receptor polypeptide is monitored. The peptides of the invention are designed to bind substantially to certain SST subtypes such as SST2 and/or SST5 with high affinity.

Receptor binding assays can be performed on cloned SS-14 receptors. Using such assays, one can generate $K_i$ values which are indicative of the concentration of a ligand necessary to occupy one-half (50%) of the binding sites on a selected amount of a receptor or the like, or alternatively, competitive assays can generate $IC_{50}$ values which are indicative of the concentration of a competitive ligand necessary to displace a saturation concentration of a target ligand being measured from 50% of binding sites.

Although an analog of octreotide has been employed to detect human tumors having high expression of SS-14 receptors through the use of positron-emission tomography, the existing SS-14 analogs do not distinguish among SST2, SST3 and SST5. In comparison, radiolabeled SS-14 analogs of the invention can be employed for similar purposes, and they are considered to be specifically useful in identifying tumors expressing SST2 and/or SST5, which tumors are then therapeutic targets for treatment with the selective analogs of the invention labeled with cytotoxic and/or radioactive agents.

The SS-14 analogs of the invention are designed to selectively interact with SST2 and/or SST5 and are useful in combating cancers, which express SST2 and/or SST5. They are also useful in scintigraphy to determine the distribution of cells and tissues expressing SST2 and/or SST5 receptor in the brain and in the endocrine and exocrine systems, and also in identifying selective functions of this receptor in the body. They are further useful for treating non-neoplastic disorders linked to SST2 and/or SST5-expressing tissues.

The invention also includes a combination of the peptide analogs of the invention and a cytotoxic drug, such as paclitaxel or any other cytotoxic moiety. The cytotoxic drug can be linked to the analog through a covalent bond or a physical encapsulation.

In general, an SS-14 analog is synthesized on a solid-phase peptide synthesizer using Fmoc chemistry. The desired compound, such as anticancer drugs paclitaxel, doxorubicin or camptothecin or the like, that is intended to be delivered to the target cells, reacts with a spacer (typically having a carboxyl terminal group) to form a covalent bond, resulting in a drug-spacer complex. Such complex is then coupled to the N-terminal of the SS-14 analog peptide on the resin to form the final product, namely, a drug-spacer-peptide complex.

The compounds of the invention (e.g., peptide analogs) may be used in radiolabeled or unlabelled form to diagnose or treat any somatostatin-responsive disease state. The compounds of the invention are particularly useful for diagnosis and/or treatment of neoplastic disorder and tumors such as, for example, neuroendocrine tumors, pituitary adenomas, pheochromocytomas, paragangliomas, medullary thyroid carcinomas, small cell and non small cell lung cancers, astrocytomas, melanomas, meningiomas, breast tumors, malignant lymphomas, renal cell carcinomas, prostate tumors, and the like. The SS-14 analogs of the invention may also be used to diagnose or to treat conditions in which angiogenesis and concomitant up-regulation of SSTs occurs. Such conditions include, for example, atherosclerosis and cellular proliferation occurring in arteries after invasive procedures such as angioplasty.

Radiolabeled SS-14 analogs of the invention are useful for such diagnoses and treatments. Radiolabeled embodiments of the analogs of the invention may be used in radioisotope guided surgery, as described in WO 93/18797 and in Woltering, et al. (1994) Surgery 116, 1139-1147. In one embodiment, a complex of a γ-emitting radionuclide and an analog of the invention is used to diagnose an SST-expressing tumor, and subsequently, a complex of β-emitting radionuclide such as $^{188}$Re or $^{186}$Re with the analog of the invention is used to treat the tumor. Other therapeutic radionuclide labels include such cytotoxic radioisotopes as scandium-47, copper-67, gallium-72, yttrium-90, iodine-125, iodine-131, samarium-153, gadolinium-159, dysprosium-165, holmium-166, ytterbium-175, lutetium-177, rhenium-186, rhenium-188, astatine-211 and bismuth-212.

For diagnostic purposes, an effective diagnostic amount of the radiolabeled analog of the invention is administered, typically intravenously. An effective diagnostic amount is defined as the amount of radiolabeled analog necessary to effect localization and detection of the label in vivo using conventional methodologies such as magnetic resonance, computerized tomography, gamma scintigraphy, SPECT, PET, and the like.

For diagnosis using scintigraphic imaging radiolabeled analogs of the invention are typically administered in a single-unit injectable dose. The labeled analog provided by the invention may be administered intravenously in any conventional medium for intravenous injection such as an aqueous saline medium, or in blood plasma medium. Generally, the unit dose to be administered has a radioactivity of about 0.01 mCi to about 100 mCi, typically 1 mCi to 50 mCi. The solution to be injected at unit dosage is from about 0.01 mL to about 10 mL. After intravenous administration, imaging in vivo can take place in a matter of a few minutes. However, imaging can take place, if desired, hours or even longer after the radiolabeled compound is injected into a subject. In most instances, a sufficient amount of the administered dose will accumulate in the area to be imaged within about 0.1 of an hour to permit the taking of scintiphotos. Any conventional method of scintigraphic imaging for diagnostic purposes can be utilized in accordance with this invention.

When the radiolabeled compounds of the invention are used for therapeutic purposes, they are radiolabeled with a therapeutically effective amount of a cytotoxic radioisotope, typically $^{188}$Re. In accordance with the invention, a therapeutically effective amount of a cytotoxic radioisotope means the total amount of each active component of the pharmaceutical composition or method that is sufficient to show a meaningful benefit to the subject, e.g., a reduction in the incidence or severity of symptoms attributed to the somatostatin-responsive disease state, as compared to that expected for a comparable group of subjects not receiving the radiotherapeutic agent of the invention. When applied to an individual active ingredient administered alone, the term refers to that ingredient alone. When applied to a combination, the term refers to combined amounts of the active ingredients that result in the therapeutic effect, whether administered in combination, serially, or simultaneously. For the purposes of this invention, radiotherapy encompasses any therapeutic effect ranging from pain palliation to tumor ablation or remission of symptoms associated with the particular somatostatin-responsive disease being treated.

When used for radiotherapy, a complex of an SS-14 analog of the invention and a cytotoxic radioisotope is administered to a subject, typically a mammal, including a human, in need of treatment for a somatostatin-responsive disease or disorder. In the radiotherapeutic method of the invention, an amount of cytotoxic radioisotope from about 5 mCi to about 200 mCi may be administered via any suitable clinical route, typically by intravenous injection or by intratumoral injection. The radiotherapeutic complex of the invention may optionally be administered in combination with a chemotherapeutic drug such as tamoxifen, cisplatin, taxol, anti-angiogenic compounds, and the like.

When unlabeled compound is used for therapy of a somatostatin-responsive disease or disorder, administration of the SS-14 analog is typically parenteral, and more commonly intravenous. The amount of unlabeled SS-14 analog administered for therapy of a somatostatin-responsive disease or disorder will depend upon the nature and severity of the condition being treated, and upon the nature of prior treatments which the subject has undergone. Ultimately, the attending physician will decide the amount of SS-14 analog with which to treat each individual subject. Initially, the attending physician will administer low doses of the SS-14 analog and observe the subject's response. Larger doses of the SS-14 analog may be administered until the optimal therapeutic effect is obtained for the subject, and at that point the dosage is not increased further. It is contemplated that the dosage of unlabelled SS-14 analog administered in the therapeutic method of the invention should be in the range of about 0.1 μg to about 100 μg compound per kg body weight. More commonly, the dosage of unlabelled SS-14 analog administered in the therapeutic method of the invention is in the range of about 0.1 μg to about 100 μg SS-14 analog per kg body weight. The unlabelled SS-14 analog of the invention may also optionally be administered in combination with a chemotherapeutic drug.

The duration of therapy, whether with a radiopharmaceutical comprising an SS-14 analog of the invention or with an unlabelled SS-14 analog of the invention, will vary, depending on the severity of the disease being treated and the condition and idiosyncratic response of each individual subject. It is contemplated that the duration of each administration of the radiopharmaceutical of the invention will be in the range of about one to about 120 minutes of continuous intravenous administration. It is contemplated that the duration of each administration of the unlabelled SS-14 analog of the invention will be in the range of about one to about 120 minutes of continuous intravenous administration. Ultimately the attending physician will decide on the appropriate duration of intravenous therapy using the labeled or unlabeled compounds of the invention, whether administered alone or in combination with other drugs.

According to one aspect of the invention, a formulation comprising one or more SS-14 analogs of the invention are provided along with a pharmaceutically acceptable carrier. The formulation provides an active dose in the range of from about 10 μg/kg body weight to about 60 μg/kg body weight of an SS-14 analog of the invention; typically about 10 μg/kg to about 20 μg/kg.

The expression "pharmaceutically acceptable" is meant to include ingredients that are compatible with an SS-14 analog of the invention as well as physiologically acceptable to a subject receiving the formation, e.g. a human, without the production of undesirable physiological effects such as nausea, dizziness, gastric upset and the like. Compositions for use according to the invention may comprise one or more carriers, excipients and/or diluents as set out below.

According to one aspect of the invention there is provided a formulation comprising one or more SS-14 analogs of the invention in a medicament for the treatment, prophylaxis or management of a disorder associated with neoplastic cells.

According to one embodiment of the invention there is provided a method for treating a human or non-human animal with a disorder associated with neoplastic cells comprising the step of administering a formulation comprising an SS-14 analog of the invention. The disorder associated with neoplastic cells may be, for example, colorectal cancer, gastric cancer, prostate cancer, cancer in the pancreas.

Non-human animals which may be treated typically include mammals, particularly livestock and domestic animals such as dogs, cats, rabbits, guinea pigs, hamsters, mice, rats, horses, goats, sheep, pigs and cows.

Depending on the mode of administration, various forms of the compositions may be used. Thus, pharmaceutical compositions may be formulated in conventional manner using readily available ingredients. The active ingredients comprising a peptide analog may be incorporated, optionally together with other active substances, with one or more conventional carriers, diluents and/or excipients, to produce conventional preparations such as tablets, pills, powders, lozenges, sachets, cachets, elixirs, suspensions, emulsions, solutions, syrups, aerosols (as a solid or in a liquid medium), ointments, soft and hard gelatine capsules, suppositories, sterile injectable solutions, sterile packaged powders, and the like.

Examples of suitable carriers, excipients and diluents, are lactose, dextrose, sucrose, sorbitol, mannitol, starches, gum acacia, calcium phosphate, alginates, tragacant, gelatine, calcium silicate, microcrystalline cellulose, polyvinylpyrrolidone, cellulose, water syrup, water, water/ethanol, water/glycol, water/polyethylene glycol, propylene glycol, methyl cellulose, methylhydroxybenzoates, propyl hydroxybenzoates, talc, magnesium stearate, mineral oil or fatty substances such as hard fat or suitable mixtures thereof. The compositions may additionally include lubricating agents, wetting agents, emulsifying agents, suspending agents, preserving agents, sweetening agents, flavoring agents, and the like. The compositions of the invention may be formulated so as to provide quick, sustained or delayed release of the active ingredient after administration to the patient by employing procedures well known in the art. Compositions may be in an appropriate dosage form, for example, as an emulsion or in liposomes, niosomes, microspheres, nanoparticles or the like.

Administration of compositions for use in the invention may take place by, any of the conventional routes, e.g. by inhalation, orally, rectally or parenterally, such as by intramuscular, subcutaneous, intraarticular, intracranial, intradermal, intraocular, intraperitoneal, intrathecal, intravenous injection although this depends on the condition to be treated. The injection may even be performed directly into an affected site (for example, by stereotaxic injection). Local administration may also be performed, e.g. at an affected site e.g. by use of a catheter or syringe. Treatment by topical application of a composition, e.g. an ointment, to the skin is also possible for appropriate conditions. Optionally administration may be performed at intervals, e.g. 2 or more applications, e.g. 2-4 applications at hourly, daily, weekly or monthly intervals, e.g. several times a day, or every 3-5 days, or at fortnightly, monthly or quarterly intervals.

The SS-14 analogs of the invention are present in the compositions from about 0.01% to about 99% by weight of the formulation, typically from about 0.1 to about 50%, for example 10%. The compositions may be formulated in a unit dosage form, e.g. with each dosage containing from about 0.01 mg to about 1 g of the active ingredient, e.g. 0.05 mg to 0.5 g, for a human, e.g. 1-100 mg. The precise dosage of the active compound to be administered and the length of the course of treatment will, of course, depend on a number of factors including for example, the age and weight of the subject, the specific condition requiring treatment and its severity, and the route of administration. Generally however, an effective dose may lie in the range of from about 10 µg/kg body weight to about 60 µg/kg body weight of an SS-14 analog of the invention, typically about 10 µg/kg to about 20 µg/kg per day, depending on the subject to be treated and the dosage form, taken as a single dose. Thus for example, an appropriate daily dose for an adult may be from 0.5 mg to 2 g per day, e.g. 1.0 to 500 mg of an SS-14 analog of the invention per day.

The peptides of the invention can be made using any number of techniques known in the art. The peptides may be synthesized by a suitable method, such as by exclusively solid-phase techniques, by partial solid-phase techniques, by fragment condensation, or by classical solution addition. For example, the techniques of exclusively solid-state synthesis are set forth in numerous textbooks including, for example, "Solid-Phase Peptide Synthesis", Stewart and Young, Freeman & Co., San Francisco, 1969. The fragment condensation method of synthesis is exemplified in U.S. Pat. No. 3,972,859 (Aug. 3, 1976). Other available syntheses are exemplified by U.S. Pat. No. 3,842,067 (Oct. 15, 1974) and U.S. Pat. No. 3,862,925 (Jan. 28, 1975).

Common to coupling-type syntheses is the protection of the labile side chain groups of the various amino acid moieties with suitable protecting groups which will prevent a chemical reaction from occurring at that site until the group is ultimately removed. Usually also common is the protection of an alpha-amino group on an amino acid or a fragment while that entity reacts at the carboxyl group, followed by the selective removal of the alpha-amino protecting group to allow subsequent reaction to take place at that location. Accordingly, it is common that, as a step in the synthesis, an intermediate compound is produced which includes each of the amino acid residues located in its desired sequence in the peptide chain with various of these residues linked to the side-action protecting groups.

Typical protecting groups, coupling agents, reagents and solvents such as, but not limited to those, listed below have the following abbreviations as used herein and in the claims. One skilled in the art would understand that the compounds listed within each group may be used interchangeably. Further, one skill in the art would know other possible protecting groups, coupling agents and reagents/solvents; these are intended to be within the scope of this invention.

Abbreviated Designation Protecting Groups
Ada Adamantane acetyl
Alloc Allyloxycarbonyl
Allyl Allyl ester
Boc tert-butyloxycarbonyl
Bzl Benzyl
Fmoc Fluorenylmethyloxycarbonyl
OBzl Benzyl ester
OEt Ethyl ester
OMe Methyl ester
Tos (Tosyl) p-Toluenesulfonyl
Trt Triphenylmethyl
Z Benzyloxycarbonyl
Abbreviated Designation Coupling Agents
BOP Benzotriazol-1-yloxytris-(dimethyl-amino) phosphonium hexafluorophosphate
DIC Diisopropylcarbodiimide
HBTU 2-(1H-Benzotriazol-1-yl)-1,1,3,3-tetramethyluronium hexafluorophosphate
PyBrOP Bromotripyrrolidinophosphonium hexafluorophosphate
PyBOP Benzotriazol-1-yl-oxy-tris-pyrrolidino-phosphonium hexafluorophosphate
TBTU O-(1,2-dihydro-2-oxo-1-pyridyl)-N,N,N',N'-tetramethyluronium tetrafluoroborate Reagents
Abbreviated Designation and Solvents
ACN Acetonitrile
AcOH Acetic acid
$Ac_2O$ Acetic acid anhydride
AdacOH Adamantane acetic acid
Alloc-Cl Allyloxycarbonyl chloride
$Boc_2O$ Di-tert butyl dicarbonate
DMA Dimethylacetamide
DMF N,N-dimethylformamide
DIEA Diisopropylethylamine
$Et_3N$ Triethylamine
EtOAc Ethyl acetate
FmocOSu 9-fluorenylmethyloxy carbonyl N-hydroxysuccinimide ester
HOBT 1-Hydroxybenzotriazole
HF Hydrofluoric acid
MeOH Methanol Mes (Mesyl) Methanesulfonyl
NMP 1-methyl-2-pyrrolidinone
nin. Ninhydrin
i-PrOH Iso-propanol
Pip Piperidine
PP 4-pyrrolidinopyridine
Pyr Pyridine
SRIF Somatotropin release inhibiting factor
SST Somatostatin receptor
TEA Triethylamine
TFA Trifluoroacetic acid
THF Tetrahydrofuran
Triflate (Trf) Trifluoromethanesulfonyl
Trf$_2$O Trifluoromethanesulfonic acid Anhydride The compounds herein described may have asymmetric centers. All chiral, diastereomeric, and racemic forms are included in the present invention. Many geometric isomers of olefins and the like can also be present in the compounds described herein, and all such stable isomers are contemplated in the present invention.

Several octapeptides were synthesized by solid-phase techniques, using a Rink-amide MBHA resin as the solid support. Generally, the linear peptide sequences are assembled via the Fmoc-strategy, and employing HBTU/HOBt/DIEA or PyBOP/HOBt/DIEA as coupling agents. Cyclization is carried with excess iodine in DMF. The peptides are then cleaved from the resin, with the simultaneous deprotection of side chains, using a cleavage mixture composed of TFA, water, and anisole. The peptides can be purified by any conventional technique including, for example, RP-HPLC and characterization by analytical HPLC and MALDI-FTMS.

The SS-14 analogs of the invention can be synthesized by classical solution synthesis, but are typically synthesized by solid-phase technique. A chloromethylated resin or a hydroxymethylated resin can be used. For example, these peptides having a free carboxyl C-terminus are typically synthesized as taught in U.S. Pat. No. 4,816,438 issued Mar. 28, 1989, the disclosure of which is incorporated herein by reference. Solid-phase synthesis is conducted in a manner to stepwise add amino acids in the chain beginning at the C-terminus. Side-chain protecting groups, which are well known in the art, are included as a part of any amino acid that has a particularly reactive side chain, and optionally may be used in the case of others such as Trp, when such amino acids are coupled onto the chain being built upon the resin. Such synthesis provides the fully protected intermediate peptidoresin. Typically a Rink amide based resin will be used. Rink Amide AM resin and Rink Amide MBHA resin are the most popular resins for the synthesis of peptide amide by Fmoc chemistry. Coupling of the first Fmoc amino acid to the resin can be achieved using the same protocol as for the solid phase peptide synthesis. Detachment of peptide amides from these supports can be affected in a single step by treatment with 95% TFA and appropriate scavengers. Thus, somatostatin analogs of the invention can be chemically synthesized in vitro. Furthermore, the SS-14 analogs of this invention can be synthesized wherein a radiolabel-binding moiety is covalently linked to the peptide during chemical synthesis in vitro, using techniques well known to those with skill in the art. Such peptides covalently-linked to the radiolabel-binding group during synthesis are advantageous because specific sites of covalent linkage are defined.

The invention has been described above, the following specific embodiments are provided to further illustrate the invention. The specific examples below are not meant to limit the scope of the invention.

EXAMPLES

Synthesis of the Peptides

The following peptides were synthesized (modified residues are shown in bold type):

1. (4-Amino)-D-Phe-c[Cys-Tyr-D-Trp-Lys-Val-Cys]-Thr-NH$_2$

2. (4-Amino)-D-Phe-c[Cys-Tyr-D-Trp-Lys-Val-Cys]-Asp-NH$_2$

3. (4-Amino)-D-Phe-c[Cys-Tyr-D-Trp-Lys-Val-Cys]-D-Thr-NH$_2$

4. (4-Amino)-D-Phe-c[Cys-Tyr-D-Trp-Lys-Val-Cys]-D-Asp-NH$_2$

5. (4-Amino)-D-Phe-c[Cys-(3-iodo)-Tyr-D-Trp-Lys-Val-Cys]-Thr-NH$_2$

6. (4-Amino-3-iodo)-D-Phe-c[Cys-Tyr-D-Trp-Lys-Val-Cys]-Thr-NH$_2$

7. (4-Amino-3-iodo)-D-Phe-c[Cys-Tyr-D-Trp-Lys-Val-Cys]-Asp-NH$_2$

8. (4-Amino-3-iodo)-D-Phe-c[Cys-(3-iodo)-Tyr-D-Trp-Lys-Val-Cys]-Thr-NH$_2$ 9. (4-Amino-3-iodo)-D-Phe-c[Cys-(3-iodo)-Tyr-D-Trp-Lys-Val-Cys]-Asp-NH$_2$ 10. D-Phe-c[Cys-Tyr-D-Trp-Lys-Val-Cys]-Asp-NH$_2$ The following notations were used: "(4-amino)-D-Phe" denotes (4-aminophenyl)-D-phenylalanine, i.e. 2-amino-3-(4-aminophenyl)-propanoic acid, "(3-iodo)-Tyr" denotes (4-hydroxy-3-iodophenyl)-L-tyrosine, i.e. 2-amino-3-(4-hydroxy-3-iodophenyl)-propanoic acid, and "(4-amino-3-iodo)-D-Phe" denotes (4-amino-3-iodophenyl)-D-phenylalanine, i.e. 2-amino-3-(4-amino-3-iodophenyl)-propanoic acid.

The following protected amino acids were used: Fmoc-Thr(tBu)-OH, Fmoc-Asp(OtBu)-OH, Fmoc-Cys(Acm)-OH, Fmoc-Val-OH, Fmoc-Lys(Boc)-OH, Fmoc-D-Trp(Boc)-OH, Fmoc-Tyr(tBu)-OH, Boc-D-Phe-OH, available from Calbiochem-Novabiochem, a division of Merck, Darmstadt, Germany. Some of the reagents (coupling agents HBTU and DIC, H-(3-iodo)-Tyr-OH, Boc-(4-amino)-D-Phe-OH) were purchased from Chem-Impex International, Wood Dale, Ill., except Boc-(4-amino-Fmoc)-D-Phe-OH, which was obtained from Bachem, Torrance, Calif. The DMF was purchased from Fisher Scientific and treated with sodium aluminosilicate molecular sieves (4 Å nominal pore diameter) obtained from Sigma and Amberlite IR120 (plus) cation exchange resin, strongly acidic. Methylene chloride (DCM) was distilled from calcium hydride. Rink amide MBHA resin and PyBOP were purchased from Calbiochem-Novabiochem, (Merck, Darmstadt, Germany). The reactions were monitored by thin-layer chromatography (TLC) carried out on EM Science Merck silica gel coated on aluminum plates (0.2 mm thickness, 60 $F_{254}$) using UV light (254 nm) as the visualizing agent and 10% ninhydrin in ethanol, bromocresol green in ethanol or 7% ethanolic phosphomolybdic acid and heat as developing agents. Silica gel 60 (230-400 mesh) purchased from EM Science was used for column chromatography.

The Kaiser test was used as a qualitative assay for the presence or absence of free amino groups during reactions on solid phase.

The peptides were constructed by manual solid phase synthesis methods, using Rink amide MBHA resin with a substitution level of 0.54 mmol/g. The activation/coupling agents used were PyBOP:HOBt:DIEA, 4:4:8 (eq), or HBTU:HOBt:DIEA, 4:4:8 (eq). All couplings and deprotections were carried out in DMF. Generally, to couple the first amino acid, 5 equivalents were used and the coupling reaction completed overnight. Following this, 4 equivalents of the commercially available protected amino acids were used, and coupling reaction times were 4 to 8 hours, allowing for differences in reactivity among amino acids. For coupling of cysteine, an activation/coupling method was chosen that did not involve use of base, namely DIC:HOBt, 1:1 (mmol), in a mixture of DCM/DMF 1/1 (vol), to minimize epimerization. Reaction time was about to 2 h.

The resin was initially swollen in DCM for at least 30 min. Deprotection of the Fmoc group from the resin and throughout the synthesis was achieved with 20% piperidine in DMF. After deprotection, the peptide-resin was washed 2 times with DMF for 1 minute, then 2 times DCM (1 min.), then again with DMF (2×1 min). After coupling, four washes with DMF were followed by washing two times with DCM, then two times with MeOH, two times with DCM, and again four times with DMF. The washing process was sometimes repeated.

Cyclization was accomplished using excess $I_2$ (10 eq) in DMF (20 mL) for 3 h. The peptide-resin was then washed 10 times with DMF, or more, until the solvent coming out of the reaction vessel was clear. To remove traces of iodine completely, a THF wash was followed by a 0.5 M $Na_2S_2O_3$ rinse, followed by DCM, MeOH, DCM, THF and DMF. Finally, the peptide-resin was rinsed twice with DCM and dried in the dessicator under high vacuum to completely remove any trace of iodine by sublimation.

For final deprotection and simultaneous cleavage of the final peptide from the resin, a cocktail composed of 9.5 mL TFA, 0.25 mL $H_2O$ and 0.25 mL anisole was used. Water and anisole were appropriate scavengers for removing t-butyl cations, which could otherwise attack the aromatic residues. The "cleavage cocktail" and the peptide-resin were separately cooled in ice, then the solution was added over the resin, and the vessel was shaken for exactly one hour at room temperature. The liquid phase was removed by filtration, and the resin washed 5 times with neat TFA. The collected filtrate containing the target peptide as a TFA salt was taken to dryness and traces of TFA were removed by azeotropic distillation with toluene, three times. The crude peptide was cooled in an ice bath, and cold ether added. A white precipitate formed, which was washed with ether, isolated by centrifugation, dissolved in water, and the aqueous solution lyophilized overnight. All the crude peptides showed one major peak by HPLC.

Synthesis of the Amino Acid Building Blocks

Boc-(4-amino)-D-Phe-OH is commercially available.

The peptidomimetic amino acid H-(3-iodo)-tyrosine (10) was commercially available. It was converted to Fmoc-(3-iodo)-tyrosine (11, Scheme 1). The reaction was carried out in the presence of 10% $NaHCO_3$, overnight.

Scheme 1: Synthesis of Fmoc-(3-I)-Tyr-OH, 11

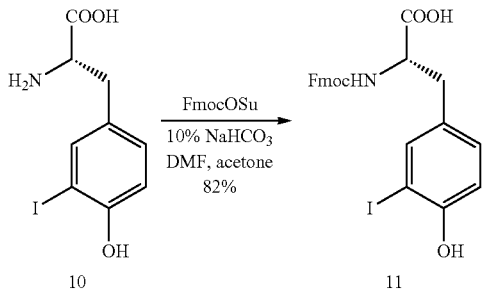

Fmoc-(3-Iodo)-tyrosine (11) To H-(3-iodo)-Tyr-OH (1.00 g, 3.26 mmol) were added 7 mL DMF and 10 mL acetone, and the suspension was cooled to 0° C. in an ice bath. After 10 min, 10% $NaHCO_3$ (w/v) (7 mL, 8.15 mmol) was added dropwise, followed by FmocOSu (1.32 g, 3.91 mmol). Another 25 mL of DMF were added, and the milky suspension was stirred vigorously at room temperature, overnight. (Note: the starting material was insoluble in water, DMF, THF, dioxane, acetonitrile, acetone, $CHCl_3$ and DCM). The solvent was removed under reduced pressure and 25 mL of water were added. The water was extracted once with EtOAc (5 mL) to remove impurities insoluble in water. The aqueous layer was cooled in an ice bath and acidified to pH approx. 1 with 2N $NaHSO_4$ and extracted five times with EtOAc (5×5 mL). The EtOAc layer was then washed twice with NaCl sat., dried over $Na_2SO_4$, filtered and concentrated to result in a clear oil. This was dried overnight on a vacuum manifold to become a white foamy solid. Chloroform (50 mL) was added, and a white precipitate formed. The precipitate (product) was filtered on a Buchner funnel, and dried overnight to yield 1.41 g (82%).

$^1$H NMR (DMF, 400 MHz): δ(ppm) 7.87 (d, J=8 Hz, 2H), 7.63 (t, J=8 Hz, 2H), 7.57 (s, 1H), 7.39 (m, 2H), 7.33 (m, 2H), 7.06 (d, J=8 Hz, 1H), 6.77 (d, J=8 Hz, 1H), 4.18 (m, 3H), 4.02 (m, 1H), 2.94 (dd, $J_1$=16 Hz, $J_2$=4 Hz, 1H), 2.72 (dd, $J_1$=16 Hz, $J_2$=12 Hz, 1H)

MS: ESI (m/z): calculated for $C_{24}H_{20}NO_5I$ [MH]$^+$ expected 530. found 530. [M+Na]$^+$ expected 552. found 552. [M-H]$^-$ expected 528. found 528

$[α]_D^{25}$=+9.04° (c=0.88, MeOH)

TLC ($CHCl_3$:MeOH:AcOH 90:10:1, bromocresol green), $R_f$=0.33.

To prepare the protected monoiodinated amino acid Boc-(4-amino-3-iodo-)-D-Phe-OH (12, Scheme 2) a simple procedure was performed, utilizing a "classical" iodination reagent iodine chloride ICl.

17

Scheme 2: Synthesis of Boc-(4-amino-3-iodo-)-D-Phe-OH, 12

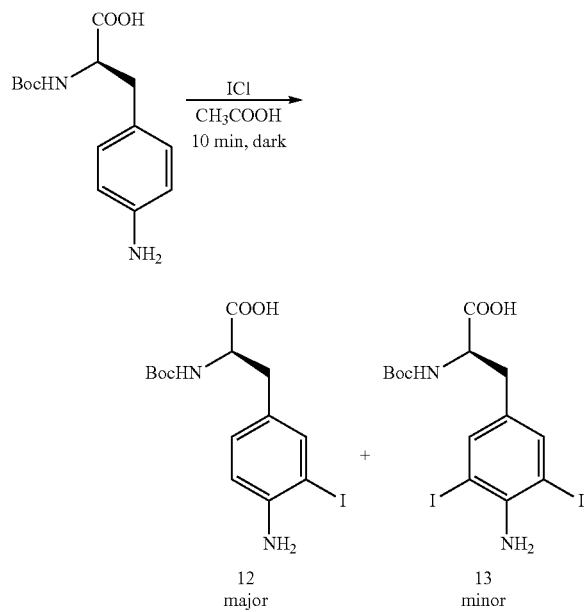

Boc-(4-amino-3-iodo)-D-Phe-OH (12) To a 100 mL round-bottomed flask were added Boc-(4-amino)-D-Phe-OH (300 mg, 1.070 mmol) and 5 mL glacial acetic acid. The flask was covered in aluminum foil. While stirring, ICl (174 mg, 1.070 mmol) was added dropwise, and the flask was immediately capped. The reaction mixture was stirred for 10 min. An excess of 0.5 N $Na_2S_2O_3$ was added to stop the reaction and quench remaining unreacted iodine (the solution turned from brown to slightly yellow). Ethyl acetate and water were added and the layers separated. The aqueous layer was back-extracted twice with ethyl acetate. The combined organic layer was further washed with 0.5 N $Na_2S_2O_3$ (3×5 mL) and saturated NaCl (3×5 mL), dried over $Na_2SO_4$ and filtered. The filtrate was concentrated and the residue dried on a vacuum manifold. The crude was purified by column chromatography using as eluent EtOAc:hexanes:AcOH 5:5:0.1 (mL) to yield 118.4 mg of product (27%). A portion of the product was further purified by HPLC and lyophilized to provide a sample (yellowish solid) for analytical purposes.

$^1$H NMR (DMSO, 400 MHz): δ 7.46 (s, 1H), 7.03 (d, J=8.0 Hz, 2H), 6.99 (d, J=8 Hz, 1H), 6.73 (d, J=8 Hz, 1H), 3.96 (m, 1H), 2.83 (dd, $J_1$=16 Hz, $J_2$=4 Hz, 1H), 2.63 (dd, $J_1$=16 Hz, $J_2$=12 Hz, 1H), 1.33 (s, 9H)

$^{13}$C NMR (DMSO, 400 MHz): δ 173.4, 155.1, 146.6, 138.5, 129.6, 127.3, 113.9, 82.9 (C-I), 77.9, 55.4, 34.9, 28.2

MS: ESI (m/z) calculated for $C_{14}H_{19}N_2O_4I$ [MH]$^+$ expected 407. found 407. [M+Na]$^+$ expected 429. found 429. [M-H]$^-$ expected 405. found 405. MALDI-FTMS: [M+Na]$^+$ expected 429.0282. found 429.0290 m. p. 68-80° C. (with decomposition)

$[α]_D^{25}$=−27.5° (c=1, MeOH) (starting material $[α]_D^{25}$=−26.9°, c=1, MeOH)

TLC (EtOAc:hexanes:AcOH 5:5:0.1 mL, ninhydrin) $R_f$=0.36

HPLC analytical: 1 mg/mL sample concentration, 10 μL injection, 10-90% B, (A: $H_2O$ with 0.1% TFA v/v; B: AcCN with 0.1% TFA v/v) at 1 mL/min over 30 min, λ=220 nm, $R_t$=18.81 min. The starting material in the same conditions exhibited an $R_t$=12.16 min.

18

The Boc protecting group survived the reaction conditions. The diiodinated Boc-(4-amino-3,5-diiodo)-D-Phe-OH was obtained as a minor product (the ratio of monoiodinated: diiodinated was about 2:1 in one instance of carrying out the reaction). This mixture was separated by column chromatography (50% yield of monoiodinated compound). The building block was then incorporated into the peptide structures with an unprotected aromatic amine, since this amine is much less reactive for amide bond formation reactions.

Synthesis of the Peptides

The peptide amides were synthesized by solid phase peptide synthesis (SPPS), following Fmoc protocols. The Rink amide MBHA resin was used as the solid support. Cleavage from this resin can be accomplished by a single step treatment with 95% TFA, providing amides in high yields and purities.

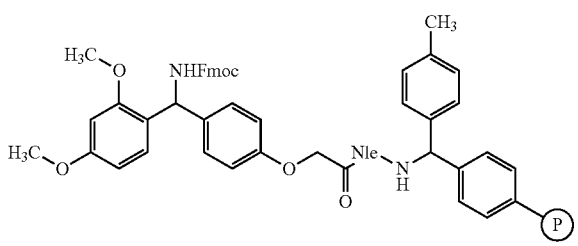

Structure of the Rink amide MBHA resin

The following protected amino acids were used: Fmoc-Thr(tBu)-OH, Fmoc-Asp(OtBu)-OH, Fmoc-Cys(Acm)-OH, Fmoc-Val-OH, Fmoc-Lys(Boc)-OH, Fmoc-D-Trp(Boc)-OH, Fmoc-Tyr(tBu)-OH, Boc-D-Phe-OH, Boc-(4-amino-Fmoc)-D-Phe-OH, and the unusual iodinated amino acids, Fmoc-(3-iodo)-Tyr-OH and Boc-(4-amino-3-iodo)-D-Phe-OH, prepared as described herein.

Coupling reagents used included PyBOP or HBTU in combination with HOBt and DIEA. Disulfide bridges were formed by reaction with excess iodine in DMF while the side chain protected peptides were on the resin. In this case, iodine functioned to remove the Acm protecting groups and oxidize the free —SH groups to form the disulfide bond.

A few illustrative examples are presented in Schemes 3, 4, 5 and 6, and detailed procedures are presented herein.

The synthesis of peptide 2 is detailed in Scheme 3. The Fmoc-protected resin was swollen in DCM and the Fmoc group deprotected using 20% piperidine/DMF. The first amino acid, Fmoc-Asp(OtBu)-OH was coupled using a pre-activated (2 min) mixture of amino acid with HBTU, HOBt and DIEA (4:4:2:8 eq relative to theoretical resin loading of 0.54 mmol/g). The remaining amino acids were added using Fmoc protocols. The last amino acid, Boc-(4-amino-Fmoc)-D-Phe-OH was introduced using DIC:HOBt (1:1 mmol) in DMF. The linear, protected peptide was then cyclized on the resin, with excess iodine (5 eq) for 3 h. The side chain Fmoc was removed with 20% piperidine in DMF. The cyclic peptide was cleaved from the resin, with the concomitant removal of the remaining protecting groups Boc and t-butyl, by treatment with TFA:$H_2O$:anisole (95:2.5:2.5%). The peptide was purified by RP-HPLC.

Scheme 3: Solid phase synthesis of peptide 2, (4-Amino)-D-Phe-c[Cys-Tyr-D-Trp-Lys-Val-Cys]-Asp-NH$_2$

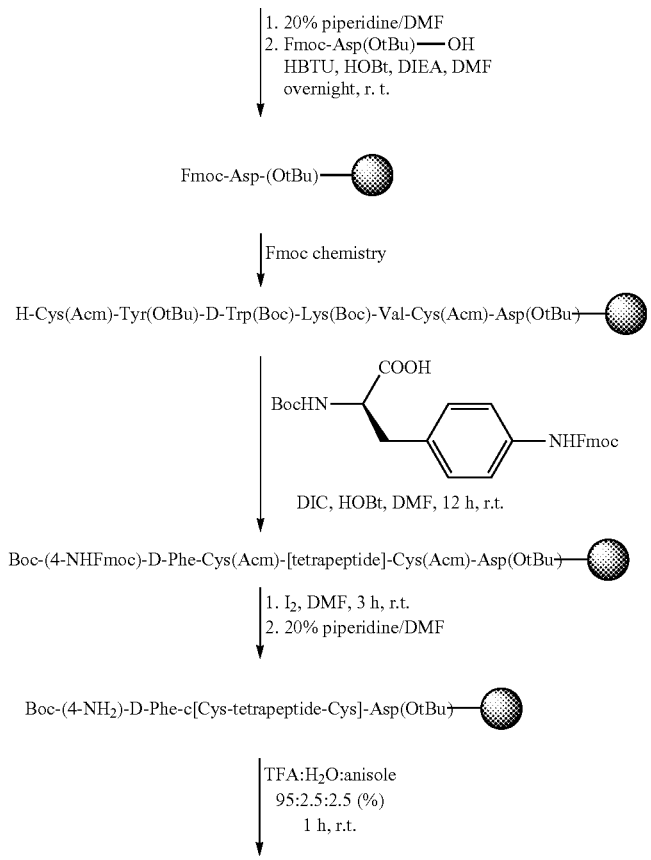

Scheme 4 illustrates the synthesis of peptide 5. After removal of the existing Fmoc protecting group from the resin, the first amino acid, Fmoc-Thr(tBu)-OH (4 eq) was coupled to the resin using PyBOP/HOBt/DIEA in DMF, (4:2:8 eq to theoretical maximal loading). Fmoc-(3-I)-Tyr-OH was coupled overnight using the same coupling mixture. The last amino acid, Boc-(4-amino-Fmoc)-D-Phe-OH, was coupled as above, using DIC/HOBt. The cyclization was effected with iodine. The remaining steps were carried out as above.

Scheme 4: Solid phase synthesis of peptide 5, (4-Amino)-D-Phe-c[Cys-(3-iodo)-Tyr-D-Trp-Lys-Val-Cys]-Thr-NH$_2$

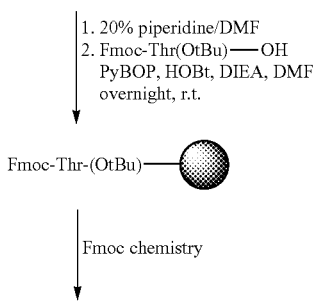

-continued

H-Cys(Acm)-(3-I)-Tyr-D-Trp(Boc)-Lys(Boc)-Val-Cys(Acm)-Thr(OtBu)—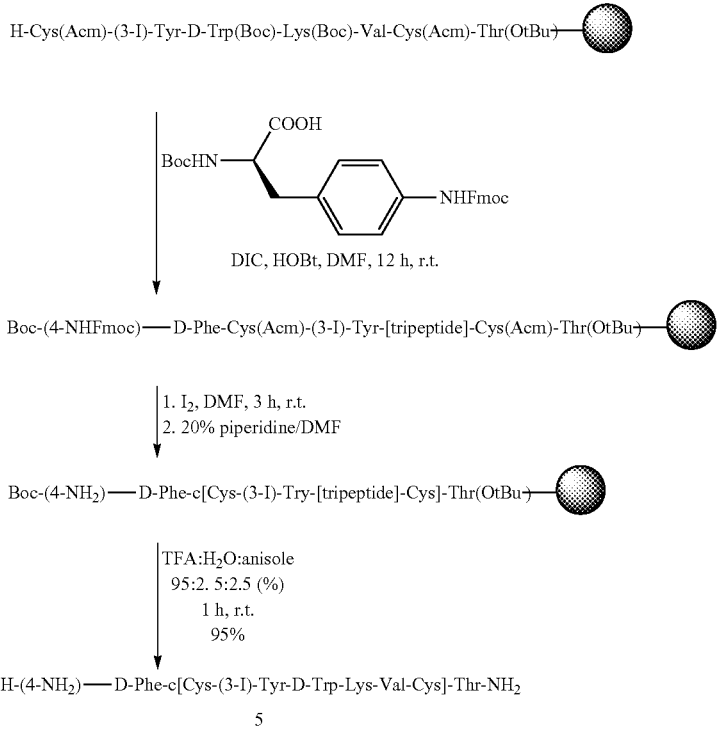

Scheme 5 illustrates the synthesis of peptide 6. The first amino acid, Fmoc-Thr(tBu)-OH was coupled as presented above. The last amino acid, Boc-(4-amino-3-iodo)-D-Phe-OH (12), was coupled to the peptide chain using DIC:HOBt (1:1 eq) in DMF, for 10 h. The peptide was cyclized with iodine, thoroughly washed, and cleaved from the resin with concomitant removal of the protecting groups.

Scheme 5: Synthesis of peptide 6, (4-Amino-3-iodo)-D-Phe-c[Cys-Try-D-Trp-Lys-Val-Cys]-Thr-NH$_2$

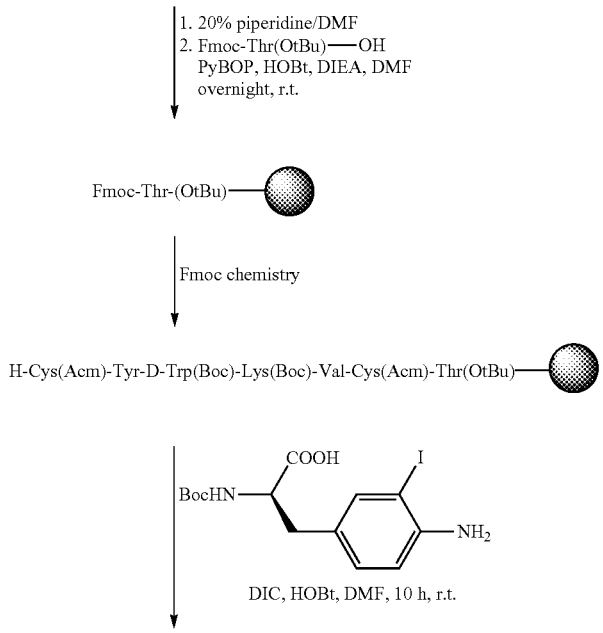

-continued

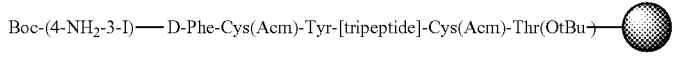

| 1. I₂, DMF, 3 h, r.t.
| 2. 20% piperidine/DMF
▼

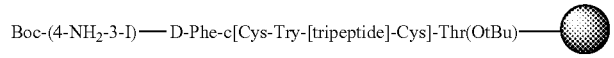

| TFA:H₂O:anisole
| 95:2. 5:2.5 (%)
|   1 h, r.t.
▼

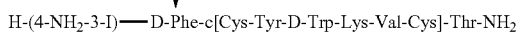

6

Scheme 6 illustrates the synthesis of peptide 8. The first amino acid, Fmoc-Thr(tBu)-OH was coupled as presented above. The Fmoc-(3-I)-Tyr-OH was also introduced as above. The last amino acid, Boc-(4-amino-3-iodo)-D-Phe-OH (12), prepared with the side chain amine free, was coupled to the peptide chain using DIC:HOBt (1:1 eq) in DMF, for 9 h. The peptide was cyclized with iodine, thoroughly washed, and cleaved from the resin with concomitant removal of the protecting groups.

Scheme 6: Solid phase synthesis of peptide 8, (4-Amino-3-iodo)-D-Phe-c[Cys-(3-iodo)-Tyr-D-Trp-Lys-Val-Cys]-Thr-NH₂

MBHA-Rink amide resin, 0.54 mmol/g

| 1. 20% piperidine/DMF
| 2. Fmoc-Thr(OtBu)—OH
|    PyBOP, HOBt, DIEA, DMF
|    overnight, r.t.
▼

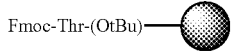

| Fmoc chemistry
▼

H-Cys(Acm)-(3-I)-Tyr-D-Trp(Boc)-Lys(Boc)-Val-Cys(Acm)-Thr(OtBu)—●

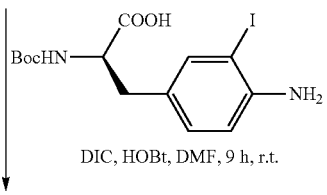

DIC, HOBt, DMF, 9 h, r.t.
▼

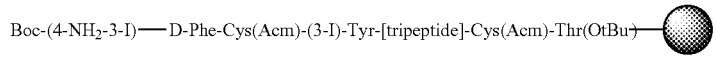

| 1. I₂, DMF, 3 h, r.t.
| 2. 20% piperidine/DMF
▼

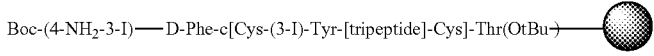

| TFA:H₂O:anisole
| 95:2. 5:2.5 (%)
|   1 h, r.t.
▼

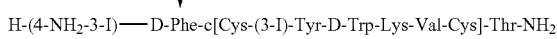

8

(4-Amino)-D-Phe-c[Cys-Tyr-D-Trp-Lys-Val-Cys]-Thr-NH$_2$ (1) was synthesized by manual SPPS, on Rink amide resin (s.l. 0.54 mmol/g), 0.2 mmol scale, in 228 mg crude yield, as noted above. A portion of the product was purified using 25% B and UV detection at λ 280 nm, to yield 16.9 mg pure peptide. Analytical conditions were: gradient 10-90% B, $R_t$=14.33 min and isocratic 26% B, $R_t$=11.13 min. MALDI-FTMS (m/z): [MH]$^+$ calcd. for $C_{50}H_{68}N_{12}O_{10}S_2$ expected 1061.4695. found 1061.4733.

(4-Amino)-D-Phe-c[Cys-Tyr-D-Trp-Lys-Val-Cys]-Asp-NH$_2$ (2) was synthesized by manual SPPS, on Rink amide MBHA resin (0.54 mmol/g), 0.37 g, 0.2 mmol scale, as noted above. The crude yield was 143.8 mg (67%). A portion of the peptide (40 mg) was purified with 25% B isocratic, and UV detection at λ 280 nm to yield 13.3 mg pure peptide. Analytical conditions were: gradient 10-90% B over 30 min, $R_t$=17.12 min and isocratic 26% B, $R_t$=8.72 min. MALDI-FTMS (m/z): [MH]$^+$ calcd. for $C_{50}H_{66}N_{12}O_{11}S_2$ expected 1075.4488. found 1075.4448.

(4-Amino)-D-Phe-c[Cys-Tyr-D-Trp-Lys-Val-Cys]-D-Thr-NH$_2$ (3) was synthesized as noted above, on 0.1 mmol scale, and 115 mg crude was obtained. Purification of a portion of material was carried out using isocratic conditions of 23% B and UV detection at λ 220 nm and 5 mg pure product were obtained. Analytical conditions: gradient 10-90% B over 30 min, $R_t$=13.58 min and isocratic 20% B, $R_t$=11.59 min. MALDI-FTMS (m/z): [MH]$^+$ calcd. for $C_{50}H_{68}N_{12}O_{10}S_2$ expected 1061.4695. found 1061.4650.

(4-Amino)-D-Phe-c[Cys-Tyr-D-Trp-Lys-Val-Cys]-D-Asp-NH$_2$ (4) was synthesized manually, as noted above, on a Rink amide MBHA resin (0.54 mmol/g), 0.19 g, 0.1 mmol scale and 88.9 mg was obtained (82%). A portion of the peptide was purified using isocratic conditions (20% B) and UV detection at λ 220 nm and 6.16 mg pure peptide was obtained. Analytical HPLC conditions: gradient 10-90% B over 30 min, $R_t$=13.59 min, and isocratic 20%, $R_t$=11.26 min. MALDI-FTMS (m/z): [MH]$^+$ calcd. for $C_{50}H_{66}N_{12}O_{11}S_2$ expected 1075.4488. found 1075.4492.

(4-Amino)-D-Phe-c[Cys-(3-iodo)-Tyr-D-Trp-Lys-Val-Cys]-Thr-NH$_2$ (5) was synthesized by manual SPPS, 0.2 mmol scale, 0.37 g resin. Fmoc-(3-I)-Tyr-OH (11) (0.26 g, 0.5 mmol, 2.5 eq), PyBOP (0.26 g, 0.5 mmol, 2.5 eq), HOBt (0.07 g, 0.5 mmol, 2.5 eq) and DIEA (0.17 mL, 1.0 mmol, 5 eq) were mixed in DMF (20 mL) and added over the deprotected peptide-resin. The resulting mixture was opalescent because the amino acid was not completely soluble. In spite of this problem, the coupling of this building block was successful. The resin was moved from the reaction vessel into a scintillation vial, and coupling carried out overnight. The resin was removed from the scintillation vial, washed on a Buchner funnel, several times, with DMF and DCM, then transferred back to the reaction vessel for subsequent couplings. The Kaiser test was used to assess the completion of the reaction and the resin was washed again with DMF (4×20 mL) and DCM (2×20 mL) and DMF (4×20 mL). The building of the peptide chain was resumed as usual. The last amino acid added was Boc-(4-amino-Fmoc)-D-Phe-OH (0.25 g, 0.5 mmol, 2.5 eq) preactivated in the presence of PyBOP (0.42 g, 0.5 mmol, 2.5 eq), HOBt (0.12 g, 0.5 mmol, 2.5 eq) and DIEA (0.21 mL, 0.5 mmol, 5 eq), in 20 mL DMF. This residue was coupled for 18 h. For cyclization, only 5 eq of iodine (0.25 g, 1.0 mmol) was used, for 3 h, in order to prevent iodination of the aromatic residues. The peptide-resin was then extensively washed as described in the general procedures and notes section, and dried for 2 h in a dessicator under high vacuum to eliminate the smallest trace of iodine. The side chain Fmoc protecting group was removed using 20% piperidine in DMF, for 1 h. The peptide resin was washed thoroughly and dried in a dessicator overnight in preparation for final deprotection/cleavage from the resin. Final treatment with TFA/H$_2$O/anisole (9.5/2.5/2.5 mL), and usual work-up resulted in 237.7 mg crude peptide (quantitative). A portion of 23 mg of the crude product was purified using isocratic conditions, 25% B, and UV detection at λ 210 and 220 nm, to yield 8.1 mg pure product. Analytical conditions: gradient 10-90% B, 30 min, $R_t$=18.04 min, isocratic 26% B, $R_t$=16.45 min. MALDI-FTMS (m/z): [MH]$^+$ calcd. for $C_{50}H_{67}IN_{12}O_{10}S_2$ expected 1187.3662. found 1187.378. [M+Na]$^+$ expected 1209.3481. found 1209.3533.

(4-Amino-3-iodo)-D-Phe-c[Cys-Tyr-D-Trp-Lys-Val-Cys]-Thr-NH$_2$ (6) was built as noted above, on 0.2 mmol scale, but only 90 mg peptide-resin were used to couple the last amino acid. The coupling mixture contained Boc-(4-amino-3-iodo)-D-Phe-OH (12) (0.044 g, 0.11 mmol, 1.5 eq), DIC (0.017 mL, 0.11 mmol, 1.5 eq) and HOBt (0.017 g, 0.11 mmol, 1.5 eq) in 10 mL DMF and the reaction was allowed to proceed for 10 h. Cyclization was carried out with iodine (0.16 g, 2.0 mmol, 10 eq) for 3 h, and the peptide-resin carefully washed and dried as illustrated above for 5. The final deprotection/cleavage procedure was accomplished in 1 h, and after lyophilization, 30.6 mg (53%) of crude peptide resulted. Purification was accomplished with 24% B in isocratic mode. The yield was 9.9 mg (13% based on theoretical loading level of the resin). Analytical HPLC: gradient 10-90% B, UV detection at λ 220 nm, $R_t$=18.9 min, isocratic 25% B, $R_t$=9.32 min. MALDI-FTMS (m/z): [MH]$^+$ calcd. for $C_{50}H_{67}IN_{21}O_{10}S_2$ expected 1187.3662. found 1187.3689, [M+Na]$^+$ expected 1209.3481. found 1209.3470.

(4-Amino-3-iodo)-D-Phe-c[Cys-Tyr-D-Trp-Lys-Val-Cys]-Asp-NH$_2$ (7) was synthesized in the same manner as compound 6. A portion of 90 mg peptide-resin was used for coupling of the final building block, which resulted in 19.4 mg (37%) crude peptide. The peptide was purified with 24% B and UV detection at λ 220 nm. The yield was 4.1 mg (7%). Analytical HPLC: gradient 10-90% B, 30 min, $R_t$=18.74 min and isocratic 22% B $R_t$=10.65 min. MALDI-FTMS (m/z): [MH]$^+$ calcd. for $C_{50}H_{65}IN_{12}O_{11}S_2$ expected 1201.3454. found 1201.3542. [M+Na]$^+$ expected 1223.3274. found 1223.3296.

(4-Amino-3-iodo)-D-Phe-c[Cys-(3-iodo)-Tyr-D-Trp-Lys-Val-Cys]-Thr-NH$_2$ (8) was synthesized as above, using 90 mg peptide resin. The couplings of the unusual building blocks were carried out as described above. The crude yield was 41 mg (64%). Purification was carried out with 25-50% B over 30 min and UV detection at λ 220 nm. The yield was 4.1 mg (7.4%). Analytical conditions: gradient 10-90% B, 30 min, $R_t$=20.4 min and isocratic 25% $R_t$=16.77 min. MALDI-FTMS (m/z): [MH]$^+$ calcd. for $C_{50}H_{66}IN_{12}O_{10}S_2$ expected 1313.2628. found 1313.2644. [M+Na]$^+$ expected 1335.2448. found 1335.2471.

(4-Amino-3-iodo)-D-Phe-c[Cys-(3-iodo)-Tyr-D-Trp-Lys-Val-Cys]-Asp-NH$_2$ (9) was synthesized by manual SPPS as described above and 38.7 mg (60%) crude was obtained. Purification: 25-40% B, 30 min, UV detection at λ 220 nm. The yield was 5 mg (7.8%). Analytical: gradient 10-90% B over 40 min, $R_t$=17.62 min, isocratic 25% B $R_t$=10.41 min. MALDI-FTMS (m/z): [MH]$^+$ calcd. for $C_{50}H_{64}I_2N_{12}O_{11}S_2$ expected 1327.2421. found 1327.2423. [M+Na]$^+$ expected 1349.224. found 1349.2274.

The target molecules were purified and analyzed by RP-HPLC using Vydac Protein Peptide $C_{18}$ columns. Column dimensions were 4.5×250 mm (90 Å silica, 5 μm) for analytical and 22×250 mm (90 Å silica, 10 μm) for preparative HPLC. The UV absorbance was monitored at 220 nm (280 nm in some cases). A binary system of water (A) and acetonitrile (B), both containing 0.1% TFA, was used throughout. Preparative HPLC was carried out at 10 mL/min flow rate, on two different instruments. One instrument was a system composed of two Waters 510 pumps and a dual wavelength UV absorbance detector. The other instrument, which was also used for analytical purposes as described below, was a Waters Millenium 2010 system, composed of two Waters 510 pumps, a 715 Ultra WISP sample injector, and a 996 photodiode array detector (PDA), operated by a NecStar PC compatible computer. Two analytical HPLC profiles of the pure compounds were obtained on the Waters Millenium PDA system, using a linear gradient of usually 10-90% acetonitrile (B) in water (A) over 30 min and an isocratic elution at 1 mL/min flow rate.

NMR spectra were obtained on a Varian HG-400 (400 MHz) and a Bruker AMX 500 (500 MHz) spectrometers. Chemical shifts ($\delta$) are reported in parts per million (ppm) relative to residual undeuterated solvent as an internal reference. The following abbreviations were used to explain multiplicities: s=singlet, d=doublet, t=triplet, q=quartet, dd=doublet of doublets, m=multiplet, b=broad.

Optical rotations were recorded on a Perkin-Elmer 241 polarimeter.

IR spectra were recorded on a Nicolet-Magna-IR 550 Series II spectrometer. Mass spectroscopic analyses (ESI, MALDI-FTMS) were carried out by the Scripps Center for Mass Spectrometry at The Scripps Research Institute, La Jolla, Calif.

Conformational Analysis-NMR and Molecular Modeling Studies. The structures of all the compounds were confirmed by ID and 2D $^1$H NMR in DMSO at 500 MHz.

NMR Spectroscopy. The samples were dissolved in DMSO-$d_6$. The NMR spectra were acquired on a Bruker AMX 500 spectrometer operating at 500 MHz and processed using FELIX2000 (Biosym/MSI, Inc.).

The $^1$H NMR data are presented in Tables 3 and 4 (chemical shifts), Tables 5 and 6 (relevant backbone NOEs) and Tables 7 and 8 (coupling constants $J_{NH-C^\alpha H}$, calculated $\phi$ angles, coupling constants $J_{C^\alpha H-C^\beta Hl}/J_{C^\alpha H-C^\beta Hh}$, calculated side-chain populations and temperature coefficients). The following notations are observed: $C^\alpha H$ and $H_\alpha$ are used interchangeably to denote the proton linked to the $\alpha$ C atom. $H_\alpha^3$ denotes the proton linked to the $\alpha$ C atom of residue 3. The subscripts 1 and h denote low- and high-field resonances, respectively.

TABLE 3

The Chemical Shifts of Compounds 1, 3, 5, 8, 10

| Analog | 1 | 3 | 5 | 8 | 10 |
|---|---|---|---|---|---|
| D-Phe$^1$NH | 8.05 | 7.95 | 7.95 | 7.98 | 7.97 |
| H$\alpha$ | 4.19 | 4.05 | 4.01 | 4.09 | 4.06 |
| H$\beta$ | 3.21/2.93 | 3.06/2.72 | 3.02/2.77 | 3.05/2.70 | 3.06/2.69 |
| H2 | 7.34 | 7.03 | 7.03 | 7.6 | 7.62 |
| H3 | 7.28 | 6.56 | 6.52 | / | / |
| H4 | 7.34-7.28 | / | / | / | / |
| H5 | 7.28 | 6.56 | 7.03 | 6.7 | 6.7 |
| H6 | 7.34 | 7.03 | 6.52 | 7.09 | 7.06 |
| Cys$^2$NH | 9.12 | 9.12 | 9.07 | 9.12 | 9.14 |
| H$\alpha$ | 5.24 | 5.24 | 5.25 | 5.25 | 5.23 |
| H$\beta$ | 2.78/2.78 | 2.80/2.80 | 2.84/2.84 | 2.83/2.83 | 2.80/2.80 |
| Tyr$^3$NH | 8.58 | 8.56 | 8.65 | 8.57 | 8.61 |
| H$\alpha$ | 4.61 | 4.59 | 4.61 | 4.65 | 4.6 |
| H$\beta$ | 2.80/2.65 | 2.79/2.64 | 2.82/2.66 | 2.82/2.67 | 2.78/2.64 |
| H2 | 6.9 | 6.89 | 6.9 | 6.9 | 7.49 |
| H3 | 6.63 | 6.6 | 6.62 | 6.62 | / |
| H5 | 6.63 | 6.6 | 6.62 | 6.62 | 6.77 |
| H6 | 6.9 | 6.89 | 6.9 | 6.9 | 6.98 |

TABLE 3-continued

The Chemical Shifts of Compounds 1, 3, 5, 8, 10

| Analog | 1 | 3 | 5 | 8 | 10 |
|---|---|---|---|---|---|
| OH | 9.17 | 9.2 | 9.2 | 9.2 | 10.1 |
| D-Trp$^4$NH | 8.66 | 8.64 | 8.67 | 8.65 | 8.73 |
| H$\alpha$ | 4.22 | 4.19 | 4.23 | 4.24 | 4.26 |
| H$\beta$ | 2.99/2.76 | 2.97/2.73 | 2.99/2.76 | 3.00/2.77 | 3.00/2.77 |
| H1 | 10.75 | 10.7 | 10.78 | 10.7 | 10.8 |
| H2 | 7.07 | 7.04 | 7.07 | 7.08 | 7.1 |
| H4 | 7.44 | 7.41 | 7.44 | 7.43 | 7.44 |
| H5 | 6.98 | 6.96 | 6.98 | 6.98 | 6.98 |
| H6 | 7.05 | 7.06 | 7.05 | 7.06 | 7.05 |
| H7 | 7.31 | 7.3 | 7.31 | 7.31 | 7.31 |
| Lys$^5$NH | 8.35 | 8.34 | 8.34 | 8.36 | 8.35 |
| H$\alpha$ | 3.92 | 3.88 | 3.95 | 3.9 | 3.91 |
| H$\beta$ | 1.71/1.24 | 1.67/1.22 | 1.72/1.21 | 1.70/1.25 | 1.67/1.18 |
| H$\gamma$ | 0.69 | 0.67 | 0.66 | 0.69 | 0.62 |
| H$\delta$ | 1.27 | 1.26 | 1.24 | 1.27 | 1.25 |
| H$\epsilon$ | 2.5 | 2.5 | 2.5 | 2.54 | 2.48 |
| NH$_2$ | 7.56 | 7.59 | 7.63 | 7.59 | 7.56 |
| Val$^6$NH | 7.54 | 7.52 | 7.54 | 7.54 | 7.48 |
| H$\alpha$ | 4.31 | 4.3 | 4.39 | 4.32 | 4.31 |
| H$\beta$ | 2.07 | 2.04 | 2.08 | 2.06 | 2.05 |
| CH$_3\gamma$ | 0.91/0.87 | 0.89/0.86 | 0.88/0.86 | 0.90/0.87 | 0.90/0.87 |
| Cys$^7$NH | 8.55 | 8.54 | 8.59 | 8.55 | 8.56 |
| H$\alpha$ | 5.03 | 5.03 | 5.09 | 5.03 | 5.03 |
| H$\beta$ | 2.80/2.80 | 2.80/2.80 | 2.79/2.79 | 2.81/2.81 | 2.80/2.80 |
| X-Asp$^8$NH | 8.1 | 8.11 | 8.16 | 8.1 | 8.1 |
| H$\alpha$ | 4.56 | 4.56 | 4.54 | 4.57 | 4.57 |
| H$\beta$ | 2.64/2.64 | 2.64/2.64 | 2.62/2.62 | 2.82/2.66 | 2.65/2.65 |
| NH$_2$ | 7.54 | 7.58/7.36 | 7.58/7.37 | 7.59/7.34 | 7.57/7.34 |

TABLE 4

The Chemical Shifts of Compounds 2, 4, 6, 7, 9

| Analog | 2 | 4 | 6 | 7 | 9 |
|---|---|---|---|---|---|
| D-Phe$^1$NH | 7.9 | 7.94 | 7.93 | 7.92 | 7.92 |
| H$\alpha$ | 4.06 | 4.08 | 4.04 | 4.03 | 4.04 |
| H$\beta$ | 3.16/2.81 | 3.06/2.78 | 3.14/2.79 | 3.12/2.75 | 3.11/2.74 |
| H2 | 7.13 | 7 | 7.12 | 7.65 | 7.63 |
| H3 | 6.67 | 6.54 | 6.7 | / | / |
| H4 | / | / | / | / | / |
| H5 | 6.67 | 6.54 | 6.7 | 6.7 | 6.7 |
| H6 | 7.13 | 7 | 7.12 | 7.1 | 7.12 |
| Cys$^2$NH | 9.27 | 9.15 | 9.29 | 9.25 | 9.27 |
| H$\alpha$ | 5.44 | 5.3 | 5.45 | 5.45 | 5.46 |
| H$\beta$ | 2.79/2.79 | 2.79/2.79 | 2.77/2.77 | 2.83/2.83 | 2.81/2.81 |
| Tyr$^3$NH | 8.67 | 8.67 | 8.7 | 8.69 | 8.71 |
| H$\alpha$ | 4.6 | 4.61 | 4.57 | 4.6 | 4.59 |
| H$\beta$ | 2.79/2.67 | 2.81/2.65 | 2.75/2.63 | 2.80/2.68 | 2.79/2.66 |
| H2 | 6.91 | 6.89 | 7.43 | 6.91 | 7.47 |
| H3 | 6.62 | 6.62 | / | 6.63 | / |
| H5 | 6.62 | 6.62 | 6.77 | 6.63 | 6.78 |
| H6 | 6.91 | 6.89 | 6.96 | 6.91 | 6.99 |
| OH | 9.22 | 9.2 | 10.1 | 9.1 | 10.1 |
| D-Trp$^4$NH | 8.7 | 8.67 | 8.77 | 8.72 | 8.79 |
| H$\alpha$ | 4.23 | 4.22 | 4.24 | 4.23 | 4.25 |
| H$\beta$ | 2.98/2.72 | 2.99/2.76 | 2.98/2.70 | 3.00/2.74 | 3.02/2.73 |
| H1 | 10.8 | 10.81 | 10.7 | 10.7 | 10.7 |
| H2 | 7.06 | 7.07 | 7.08 | 7.07 | 7.09 |
| H4 | 7.41 | 7.43 | 7.41 | 7.41 | 7.41 |
| H5 | 6.96 | 6.97 | 6.97 | 6.98 | 6.98 |
| H6 | 7.04 | 7.04 | 7.04 | 7.06 | 7.05 |
| H7 | 7.3 | 7.3 | 7.29 | 7.31 | 7.33 |
| Lys$^5$NH | 8.37 | 8.37 | 8.38 | 8.38 | 8.37 |
| H$\alpha$ | 3.94 | 3.92 | 3.95 | 3.94 | 3.93 |
| H$\beta$ | 1.74/1.25 | 1.69/1.22 | 1.70/1.17 | 1.73/1.22 | 1.69/1.18 |
| H$\gamma$ | 0.66 | 0.67 | 0.6 | 0.66 | 0.59 |
| H$\delta$ | 1.26 | 1.26 | 1.26 | 1.26 | 1.23 |
| H$\epsilon$ | 2.55 | 2.5 | 2.52 | 2.52 | 2.5 |
| NH$_2$ | 7.67 | 7.68 | 7.6 | 7.59 | 7.58 |
| Val$^6$NH | 7.48 | 7.56 | 7.47 | 7.52 | 7.46 |
| H$\alpha$ | 4.43 | 4.36 | 4.45 | 4.42 | 4.43 |
| H$\beta$ | 2.04 | 2.08 | 2.01 | 2.03 | 2.01 |

TABLE 4-continued

The Chemical Shifts of Compounds 2, 4, 6, 7, 9

| Analog | 2 | 4 | 6 | 7 | 9 |
|---|---|---|---|---|---|
| $CH_3\gamma$ | 0.88/0.84 | 0.91/0.87 | 0.88/0.87 | 0.88/0.86 | 0.89/0.86 |
| $Cys^7 NH$ | 8.63 | 8.63 | 8.64 | 8.64 | 8.66 |
| $H\alpha$ | 5.3 | 5.28 | 5.31 | 5.31 | 5.3 |
| $H\beta$ | 2.79/2.79 | 2.94/2.84 | 2.75/2.75 | 2.82/2.82 | 2.81/2.81 |
| $X-Thr^8 NH$ | 8.19 | 8.01 | 8.2 | 8.18 | 8.18 |
| $H\alpha$ | 4.28 | 4.21 | 4.29 | 4.27 | 4.28 |
| $H\beta$ | 4.04 | 4.03 | 4.03 | 4.03 | 4.02 |
| $CH_3\gamma$ | 1.04 | 1.05 | 1.05 | 1.04 | 1.03 |
| OH | 5.2 | 5.38 | 5.2 | 5.23 | 5.18 |
| $NH_2$ | 7.63/7.37 | 7.50/7.28 | 7.67/7.37 | 7.62/7.34 | 7.64/7.34 |

TABLE 5

Observed Backbone NOEs[a] for Compounds 1, 2, 3, 4 and 5

| NOE | 1 | 2 | 3 | 4 | 5 |
|---|---|---|---|---|---|
| $H_\alpha^1$—$NH^2$ | s | s | s | s | s |
| $H_\alpha^2$—$NH^2$ | m | m | m |   | m |
| $H_\alpha^2$—$NH^3$ | s | s | m |   | s |
| $H_\alpha^2$—$H_\alpha^7$ | m | m | m |   | m |
| $H_\alpha^3$—$NH^3$ |   |   |   |   |   |
| $H_\alpha^3$—$NH^4$ |   |   |   |   |   |
| $H_\alpha^4$—$NH^4$ | m | m | m | m | m |
| $H_\alpha^4$—$NH^5$ | s | s | s | s | s |
| $H_\alpha^5$—$NH^5$ | m | m | m | m | m |
| $H_\alpha^5$—$NH^6$ | m | m | m | m | m |
| $NH^5$—$NH^6$ | m | m | m | m | m |
| $H_\alpha^6$—$NH^6$ | m | m | m | m | m |
| $H_\alpha^6$—$NH^7$ | s | s | s | s | s |
| $NH^6$—$NH^3$ |   | m | m | m | m |
| $H_\alpha^7$—$NH^7$ | m | m | m |   | m |
| $H_\alpha^7$—$NH^8$ | s | s | s | s | s |
| $NH^7$—$NH^8$ | m |   | w |   | m |
| $H_\alpha^8$—$NH^8$ |   | m | m | m | m |

[a]The NOEs corresponding to distances ≤2.5 Å are classified as strong (s); the NOEs corresponding to distances >2.5 and ≤3.5 Å are classified as medium (m); the NOEs corresponding to distances >3.5 and ≤4.5 Å are classified as weak (w).

TABLE 6

Observed Backbone NOEs for Compounds 6, 7, 8, 9 and 10

| NOE | 6 | 7 | 8 | 9 | 10 |
|---|---|---|---|---|---|
| $H_\alpha^1$—$NH^2$ | s |   | s | s | s |
| $H_\alpha^2$—$NH^2$ | m | m | m | s | m |
| $H_\alpha^2$—$NH^3$ | s | s | s | s | s |
| $H_\alpha^2$—$H_\alpha^7$ | m | m | m | m | m |
| $H_\alpha^3$—$NH^3$ |   |   |   |   | m |
| $H_\alpha^3$—$NH^4$ |   |   |   |   | s |
| $H_\alpha^4$—$NH^4$ | m | m | m | m | m |
| $H_\alpha^4$—$NH^5$ | s | s | s | s | s |
| $H_\alpha^5$—$NH^5$ | m | m | m | m | m |
| $H_\alpha^5$—$NH^6$ | m | m | m | m | m |
| $NH^5$—$NH^6$ | m | m | m | m | m |
| $H_\alpha^6$—$NH^6$ | m | m | m | m | m |
| $H_\alpha^6$—$NH^7$ | s | s | s | s | s |
| $NH^6$—$NH^3$ | m | m | w | m | m |
| $H_\alpha^7$—$NH^7$ | m | m | m |   | m |
| $H_\alpha^7$—$NH^8$ | s | s | s | s | s |
| $NH^7$—$NH^8$ |   |   |   | m | m |
| $H_\alpha^8$—$NH^8$ | m | m | m | m | m |

[a]The NOEs corresponding to distances ≤2.5 Å are classified as strong (s); the NOEs corresponding to distances >2.5 and ≤3.5 Å are classified as medium (m); the NOEs corresponding to distances >3.5 and ≤4.5 Å are classified as weak (w).

TABLE 7

Coupling Constants $J_{NH-C^\alpha H}$, Calculated φ values[a], $J_{C^\alpha H-C^\beta H}$ Coupling Constants, Side Chain Populations[a] and Temperature Coefficients (−ppb/K) of the Amide Protons[b] in Compounds 1, 2-5.

| Residue | $J_{NH-C^\alpha H}$ | Calculated φ angles | $J_{\alpha\beta l}/J_{\alpha\beta h}$ | Side-chain population $g^-$, t, $g^+$ | −Δppm/K NH |
|---|---|---|---|---|---|
| 1 | | | | | |
| D-Phe[1] | / | / | 5.70/7.84 | 0.23, 0.54, 0.23 | / |
| Cys[2] | / | / | / | / | 6.8 |
| Tyr[3] | 8.22 | −146, −94 | 9.44/6.50 | 0.35, 0.47, 0.18 | 4.3 |
| D-Trp[4] | 4.38 | 171, 69, −102, −18 | 9.05/6.78 | 0.20, 0.44, 0.36 | 6.4 |
| Lys[5] | 8.22 | −146, −94 | ~14, too small | 1, f(t)~f($g^+$) | 4 |
| Val[6] | 9.64 | −131, −109 | 8.81 | 0.57 | 0.9 |
| Cys[7] | 9.32 | −136, −104 | / | / | 5.5 |
| Asp[8] | 7.12 | −154, −86, 79, 40 | / | / | 3.3 |
| 2 | | | | | |
| 4-amino-D-Phe[1] | / | / | 5.68/8.66 | 0.30, 0.49, 0.21 | / |
| Cys[2] | 9.33 | −136, −104 | / | / | 7.7 |
| Tyr[3] | 8.71 | −142, −97 | 8.83/7.25 | 0.51, 0.36, 0.13 | 3.5 |
| D-Trp[4] | 6 | −90, −30, 79, 161 | 8.52/6.78 | 0.20, 0.48, 0.31 | 6.5 |
| Lys[5] | 7.26 | −153, −87, 78, 42 | 4.41/11.0 | 0.77, 0.21, 0.07 | 4.3 |
| Val[6] | 8.87 | −140, −99 | 6.21 | 0.32 | 0.6 |
| Cys[7] | 9.25 | −136, −103 | / | / | 5.8 |
| Thr[8] | 8.24 | −146, −94 | 5.19 | 0.24 | 5.3 |

TABLE 7-continued

Coupling Constants $J_{NH-C^IH}$, Calculated φ values$^a$, $J_{C^IH-C^\beta H}$ Coupling Constants, Side Chain Populations$^a$ and Temperature Coefficients (−ppb/K) of the Amide Protons$^b$ in Compounds 1, 2-5.

| Residue | $J_{NH-C^\alpha H}$ | Calculated φ angles | $J_{\alpha\beta l}/J_{\alpha\beta h}$ | Side-chain population $g^-$, t, $g^+$ | −Δppm/K NH |
|---|---|---|---|---|---|
| 3 | | | | | |
| 4-amino-D-Phe$^1$ | / | / | 6.08/8.59 | 0.27, 0.49, 0.21 | |
| Cys$^2$ | 9.49 | −133, −106 | / | / | 7.1 |
| Tyr$^3$ | 8.63 | −142, −97 | 6.73/8.78 | / | 4.3 |
| D-Trp$^4$ | 4.56 | −101, −19, 70, 170 | 7.00/8.23 | 0.22, 0.45, 0.33 | 6.5 |
| Lys$^5$ | 7.67 | −150, −90, 72, 48 | 4.89/10.54 | 0.72, 0.21, 0.07 | 4.2 |
| Val$^6$ | 9.54 | −132, −107 | 4.45 | 0.17 | 0.2 |
| Cys$^7$ | 9.34 | −135, −304 | / | | 5.5 |
| Asp$^8$ | 8.06 | −147, −93 | / | | 4.3 |
| 4 | | | | | |
| 4-amino-D-Phe$^1$ | / | / | 5.58/8.70 | 0.30, 0.20, 0.50 | / |
| Cys$^2$ | 8.86 | −141, −99 | / | / | 6.8 |
| Tyr$^3$ | 8 | −148, −92 | 7.85/6.10 | 0.42, 0.25, 0.33 | 4.7 |
| D-Trp$^4$ | 6.44 | −86, −34, 82, 158 | 9.26/6.38 | 0.17, 0.55, 0.27 | 7.15 |
| Lys$^5$ | 8.4 | −145, −95 | ~14, too small | 1, f(t)~f($g^+$) | 3.9 |
| Val$^6$ | 9.01 | −139, −101 | 7.14 | 0.41 | 0.8 |
| Cys$^7$ | 9.47 | −134, 106 | 4.62/10.43 | 0.71, 0.18, 0.10 | 5.9 |
| D-Thr$^8$ | 8.6 | 97, 143 | 4.8 | 0.2 | 5.3 |
| 5 | | | | | |
| D-Phe$^1$-NH$_2$ | / | / | 6.12/918 | 0.20, 0.25, 0.55 | / |
| Cys$^2$ | 8.69 | −142, −98 | / | / | 6.5 |
| Tyr$^3$ | 7.74 | −150, −90, 70, 50 | 7.85/6.02 | overlap | 3.7 |
| D-Trp$^4$ | 4.15 | −104, −16, 173, 67 | 8.16/7.14 | 0.20, 0.49, 0.32 | 5.3 |
| Lys$^5$ | 8.12 | −147, −93 | ~14, too small | 1, f(t)~f($g^+$) | 3.8 |
| Val$^6$ | 9.82 | −128, −112 | 8.17 | 0.35 | 0.5 |
| Cys$^7$ | 9.62 | −132, −108 | / | / | 5 |
| D-Asp$^8$ | 7.9 | −66, −54, 91. 148 | / | overlap | 3.22 |

$^a$See NMR spectroscopy experimental section.
$^b$In DMSO solution, amide protons that have temperature coefficients (−Δppb/K) in the range of 0-2.0 −ppb/K are considered to be involved in an intramolecular hydrogen bonding or are solvent-shielded. Values greater than 4.0 −ppb/K are considered to be completely solvent exposed.

TABLE 8

Coupling Constants $J_{NH-C^IH}$, Calculated φ values$^a$, the Coupling Constants $J_{C^IH-C^\beta H}$, the Side Chain Populations$^a$ and Temperature Coefficients (−ppb/K) of the Amide Protons$^b$ for Compounds 6-10

| Residue | $J_{NH-C^\alpha H}$ | Calculated φ angles | $J_{\alpha\beta l}/J_{\alpha\beta h}$ | Side-chain population $g^-$, t, $g^+$ | −Δppm/K NH |
|---|---|---|---|---|---|
| 6 | | | | | |
| 3-iodo-4-amino-D-Phe$^1$ | / | / | 6.20/8.78 | 0.23, 0.51, 0.26 | / |
| Cys$^2$ | 9.12 | −138, −102 | / | / | 7.4 |
| 3-iodo-Tyr$^3$ | 8.03 | −148, −92 | 8.13/6.21 | 0.26, 0.45, 0.30 | 4 |
| D-Trp$^4$ | 5.11 | −97, −23, 73, 167 | 8.94/7.45 | 0.10, 0.52, 0.38 | 5.6 |
| Lys$^5$ | 8.77 | −141, −98 | 4.62/10.3 | 0.70, 0.20, 0.11 | 4 |
| Val$^6$ | 9.98 | −122, −117 | 6.95 | 0.4 | 1.8 |
| Cys$^7$ | 9.48 | −134, −106 | / | / | 6 |
| Thr$^8$ | 8.6 | −143, −97 | 4.39 | 0.16 | 5 |
| 7 | | | | | |
| 3-iodo-4-amino-D-Phe$^1$ | / | / | 6.43/9.19 | 0.32, 0.47, 0.21 | / |

TABLE 8-continued

Coupling Constants $J_{NH-C^\alpha H}$, Calculated $\phi$ values[a], the Coupling Constants $J_{C^\alpha H-C^\beta H}$, the Side Chain Populations[a] and Temperature Coefficients (-ppb/K) of the Amide Protons[b] for Compounds 6-10

| Residue | $J_{NH-C^\alpha H}$ | Calculated $\phi$ angles | $J_{\alpha\beta'}/J_{\alpha\beta h}$ | Side-chain population $g^-$, t, $g^+$ | $-\Delta$ppm/K NH |
|---|---|---|---|---|---|
| Cys² | 9.34 | −136, −104 | / | / | 5.8 |
| Tyr³ | 8.54 | −143, −96 | 7.90/6.59 | 0.32, 0.39, 0.29 | 4.3 |
| D-Trp⁴ | 6.24 | −88, −32, 80, 160 | 7.88/6.23 | 0.32, 0.42, 0.26 | 6.3 |
| Lys⁵ | 8.56 | −143, −97 | ~14, too small | 1, f(t)~f(g⁺) | 4 |
| Val⁶ | 9.31 | −136, −104 | 6.19 | 0.33 | 0.5 |
| Cys⁷ | 9.01 | −139, −101 | / | / | 5.5 |
| Thr⁸ | 8.22 | −146, −94 | 4.7 | 0.19 | 3.6 |
| 8 | | | | | |
| 3-iodo-4-amino-D-Phe1 | / | / | 5.35/8.55 | 0.34, 0.48, 0.17 | / |
| Cys2 | 8.91 | −140, −100 | / | / | 5.8 |
| Tyr3 | 8.1 | −147, −93 | 8.07/8.58 | 0.43, 0.50, 0.07 | 4.3 |
| D-Trp4 | 4.46 | 171, 69, −102, −18 | 8.56/6.81 | 0.20, 0.49, 0.32 | 6.3 |
| Lys5 | 8.37 | −145, −95 | ~14, too small | 1, f(t)~f(g+) | 4 |
| Val6 | 9.12 | −138, −102 | 6.33 | 0.34 | 0.5 |
| Cys7 | 9.28 | −136, −104 | / | / | 5.5 |
| Asp8 | 8.27 | −146, −94 | 6.85/6.44 | 0.35, 0.39, 0.26 | 3.6 |
| 9 | | | | | |
| 3-iodo-4-amino-D-Phe1 | / | / | 6.28/8.98 | 0.37, 0.44, 0.19 | / |
| Cys2 | 9.12 | −138, −102 | / | / | 7 |
| 3-iodo-Tyr3 | 7.9 | −149, −91, 66, 53 | 7.91/6.88 | 0.31, 0.40, 0.29 | 4 |
| D-Trp4 | 4.86 | −99, −21, 72, 168 | 8.94/7.22 | 0.12, 0.52, 0.35 | 5.8 |
| Lys5 | 8.51 | −144, −96 | ~14, too small | 1, f(t)~f(g+) | 4.1 |
| Val6 | 9.53 | −133, −107 | 8.15 | 0.5 | 0.6 |
| Cys7 | 8.12 | −138, −102 | / | / | 5.7 |
| Thr8 | 8.51 | −144, −96 | 4.95 | 0.21 | 5.1 |
| 10 | | | | | |
| 3-iodo-4-amino-D-Phe1 | / | / | 5.70/8.70 | 0.21, 0.56, 0.23 | / |
| Cys2 | 9.49 | −134, −106 | / | / | 5.7 |
| 3-iodo-Tyr3 | 7.81 | −149, −91, −69, 51 | 8.62/4.64 | / | 3.9 |
| D-Trp4 | 5.02 | 167, 73, −97, −23 | 8.70/6.30 | 0.23, 0.50, 0.27 | 5.8 |
| Lys5 | 8.37 | −145, −95 | ~14, too small | 1, f(t)~f(g+) | 4 |
| Val6 | 9.4 | −135, −105 | 8.55 | 0.54 | 0.1 |
| Cys7 | 8.93 | −140, −100 | / | / | 5.4 |
| Asp8 | 8.37 | −145, −95 | / | / | 3.6 |

[a],[b] as in Table 7

Tables 7 and 8 show the $\chi_1$ rotamer populations computed on the basis of the measured $J_{C^\alpha H-C^\beta H}$ coupling constants using the three-state rotamer model. The side chain conformations which are relevant for somatostatin-like binding activity are those of D-Phe¹, D-Trp⁴, and Lys⁵. For the residues in position 1, in compounds 1, 2, 3, 6, 7, 8, 9 and 10 the most populated $\chi_1$ rotamer is consistently the trans. This conformation allows the aromatic side chain of the D-Phe¹ to be located in the vicinity of the bridging disulfide region. There are some minor differences between these analogs regarding the orientation of the D-Phe¹ aromatic side chain relative to the disulfide bridge. In most analogs this side-chain adopts a trans orientation, which results in close spatial proximity of the disulfide bridge and the aromatic ring. This orientation has also been reported for Sandostatin®. In the analogs with D configuration at $C^\alpha$ in position 8, the side chain prefers a g⁺ orientation, which brings the aromatic ring of position 1 far from the disulfide bridge.

As for the side chains of D-Trp⁴ and Lys⁵, the $\chi_1$ rotamers in the bioactive compounds are trans and g⁻, respectively, as shown in Tables 7 and 8. These rotamers allow a close proximity between the side chains of D-Trp⁴ and Lys⁵, which is confirmed by the upfield shift observed for the $C^\gamma H$ resonances of Lys⁵, caused by the D-Trp⁴ aromatic ring current. These conformational preferences are very similar to those found for the parent compound Sandostatin®.

These studies demonstrate that all analogs adopt conformations very similar to each other. Furthermore, the conformations of these compounds are very similar to those adopted by Sandostatin® and its active analogs. The backbone conformation can be described as an antiparallel β-sheet containing a type II' β-turn with D-Trp in the i+1 position, and most structures are folded about Phe³ and Val⁶.

In the molecules containing iodine, there seems to be a preference for the aromatic side chains to situate themselves close to one another. This tendency may create a large hydrophobic area, which may bind to a specific hydrophobic zone on the receptors. Alternatively, the presence of the large, hydrophobic iodine may induce a conformation that favors binding to receptors hsst2 and hsst5, but not hsst3.

The conformational analysis data show that the analogs studied have great similarity among each other and compared to Sandostatin®. Medium strength NOEs between the NH protons of Val⁶ and Lys⁵ and the absence of NOEs between the NH protons of Lys⁵ and D-Trp⁴ suggest a type II' β-turn with D-Trp in the i+1 position for these compounds. This is consistent with the low temperature coefficients of the Val⁶NH protons and with strong sequential NOEs between Lys⁵NH and D-Trp⁴H$_\alpha$, medium strength NOEs between Val⁶NH and Lys⁵H$_\alpha$, and medium strength NOEs between Lys⁵NH and Lys⁵H$_\alpha$.

The β-sheet-like conformation found for the other parts of the backbone is consistent with the $J_{NH-C^\alpha H}$ coupling constants and with the high temperature coefficients measured for the NH⁴ and NH⁷ resonances (Tables 7 and 8). These temperature coefficients are in full agreement with the solvent exposure expected for NH⁴ and the NH⁷ protons in the antiparallel β-sheet structure. The β-sheet-like conformation is also supported by the strong sequential C$^\alpha$H—NH NOEs (see the H$_\alpha^2$—NH³, the H$_\alpha^3$—NH⁴, the H$_\alpha^6$—NH⁷ and the H$_\alpha^7$—NH⁸ NOEs, and by the H$_\alpha^2$—H$_\alpha^7$ NOE (Tables 5 and 6). The H$_\alpha^2$—H$_\alpha^7$ NOE also indicates that the disulfide bridge is a good mimetic of a β-VI turn for which this type of H$_\alpha$ to H$_\alpha$ NOE is typically observed.

The conformational analysis of Sandostatin® suggested that this molecule adopts multiple conformations such as a β-sheet structure and conformations which contain a helical fold in the C-terminal portion. All the analogs studied showed the NH⁶—NH³ NOEs consistent with a β-sheet structure, but only the analogs with Asp in position 8 showed the NH⁷—NH⁸ NOEs, characteristic for a partial helical fold in this region. These NOEs indicate that the partially helical structures are more populated in the compounds containing an Asp residue, than in the compounds with a Thr residue in position 8.

NMR spectroscopy. The resonance assignments were carried out using ¹H NMR, TOCSY (total correlation spectroscopy) and ROESY (rotating frame nuclear Overhauser) experiments. The TOCSY experiment is used to assign the spin systems and the ROESY experiment allows the sequential assignments of the amino acid spin systems from observed sequential NOE connectivities $d_{C^\alpha H-HN}$ or $d_{HN-HN}$, or possibly $d_{C^\beta H-HN}$.

The $J_{NH-C^\alpha H}$ and $J_{C^\alpha H-C^\beta H}$ coupling constants were obtained from 1D spectra and from sections of cross-peaks, obtained from the DQF-COSY spectra. Measured NH-C$^\alpha$H and C$^\alpha$H—C$^\beta$H coupling constants allowed us to estimate the ranges of φ and χ₁ torsion angles. The vicinal coupling constant $J_{NH-C^\alpha H}$ is related to torsion angle φ (which represents the rotational state around skeletal single bond NH—C$^\alpha$H) by a Karplus-type equation:

$$J_{NH-C^\alpha H} = A\cos^2|\phi \pm 60°| - B\cos|\phi \pm 60°| + C$$

where:
(+) is for the D configuration and (−) is for the L configuration, respectively and coefficients: A=8.6, B=1.0 and C=0.4.

The values of coupling constants $J_{NH-C^1 H}$ and the corresponding estimated φ angle values are listed in Tables 7 and 8.

The fraction of the individual conformers $f_1$ ($\chi_1$) may be estimated by using the following conventional expressions:
(a) for the L residue $f(g^-) = (J_{H1-H\theta1} - J_G)/(J_T - J_G)$ for the gauche (−) conformation $f(t) = (J_{H1-H\theta2} - J_G)/(J_T - J_G)$ for the trans conformation $f(g^+) = 1 - [f(g^-) + f(t)]$ for the gauche(+) conformation (b) and for the D residue:

$f(t) = (J_{H1-H\theta2} - J_G)/(J_T - J_G)$ for the trans conformation.

$f(g^+) = (J_{H1-H\theta1} - J_G)/(J_T - J_G)$ for the gauche (+) conformation $f(g^-) = 1 - [(f(g^-) + f(t)]$ for the gauche (−) conformation.

The values $J_T$=13.56 Hz and $J_G$=2.60 Hz for trans and gauche coupling were used to calculate the rotameric populations of non aromatic residues, while the values $J_T$=13.85 Hz and $J_G$=3.55 Hz were used for the aromatic residues.

Different intensities of the amide to β proton NOEs and the α to β proton NOEs, from ROESY spectra, allow the assignment of the diastereotopic β protons. Once the diastereotopic methylene β protons are assigned, the rotameric population f(t), f(g⁺), f(g⁻) can be calculated using the previous equations. However, in some cases because of the overlapping of the β protons or the absence of significant NOEs, the diastereotopic assignment cannot be performed. In such cases it is not possible to distinguish between the two possible rotameric populations.

Molecular modeling. The computer simulations were carried out on an SGI IRIX 6.5 workstation and Challenge computer (Silicon Graphics). The Insight II and DISCOVER programs were used for the molecular mechanics, dynamics calculations and visualizations.

Initially, 200 structures were generated using DGII/InsightII, followed by a restrained minimization with a CVFF91 force field and the Newton-Ralphson VA09A algorithm with a convergence criterion of 0.001 Kcal/molÅ. All the calculations were carried out in vacuo and a distance dependent dielectric constant was used to take into account the solvent effects. In the simulations, the peptide bonds were maintained in the trans conformation.

The torsion angles, the NOE distances and hydrogen-bonding patterns of these structures were compared with the values derived from NMR measurements. A Karplus-type equation was used to compute the torsion angles consistent with the measured $J_{NH-C^\alpha H}$ coupling constants, and an error of ±30° was tolerated. In the case of selections based on the hydrogen bonds, structures were retained in which NH protons with a temperature coefficient greater than 2.0-ppb/K were considered to be involved in a hydrogen bond. Structures not consistent with these experimental constraints were discarded. A cut-off of 10 Kcal/mol above the lowest energy conformer was used to sort out unrealistically high-energy conformations of the remaining structures.

A cluster analysis was performed by first extracting the lowest energy conformer out of all the conformations under investigation. These conformers served as a "seed" to grow a cluster as long as the selected torsion was within a 30° interval. The analysis then iteratively searched for the next high-energy cluster until the highest family was found. Prior to every molecular dynamics simulation, the system was equilibrated with 3 ps initialization dynamics. In attempts to carry out a thorough search of the accessible conformational space, the lowest energy conformation of the clusters was subjected to 500 ps of restrained molecular dynamics at 1000 K with a step size of 1 fs. The conformers that were consistent with experimental data were subjected to the same cluster analysis as described above. Finally, the lowest energy structure of each cluster was chosen as the preferred conformation in solution of the somatostatin analogs.

Unrestrained molecular dynamics simulations at 300 K with a distance-dependent dielectric constant of 1 were carried out to investigate the equilibrium between these preferred conformations. The selected conformers were first submitted to 3 ps of equilibrium, followed by a step size of 1 fs for a 5 ns simulation. Structures were collected every 10 ps. During this process, conformational interchanges were observed.

Biological Activity

The binding assays can be executed on membranes from CC531 cells (hsst2) and CHO-K1 cells (hsst1, 3 and 5), transfected with individual human somatostatin receptor subtypes. The functional assays—inhibition of growth hormone and prolactin secretion—cab be carried out with dispersed rat pituitary cells.

Female Wistar rats (Harlan, The Netherlands), weighing 180-200 g, are kept in an artificially illuminated room (08.30-20.30 h) with food and water ad libitum. The animals are killed between 09.00 and 10.00 h by decapitation. The pituitary glands are removed within 5 minutes after killing, the neuro-intermediate lobe is discarded and the anterior lobes are collected in calcium, magnesium—Hank's balanced salt solution (HBSS) supplemented with 1% fetal calf serum (FCS), penicillin (100 U/mL), streptomycin (100 μg/mL), fungizone (0.5 μg/mL) and sodium carbonate (0.4 μg/L final concentration).

Female anterior pituitary cells are isolated with dispase (see, e.g., Oosterom et al., J Endocrinol. 100(3):353-60, 1984). The dispersed cells are seeded at a density of 0.5–1× $10^5$ cells per well in multiwell plates. The culture medium is Eagle's Minimum Essential Medium with Earle's salts supplemented with a 1-fold excess of nonessential amino acids, 1 mM sodium pyruvate, 2 mM L-glutamine, penicillin (100 U/mL), streptomycin (100 μg/mL), and fungizone (0.25 μg/mL) and 10% fetal calf serum (Invitrogen, Breda, the Netherlands). Media and supplements are obtained from Gibco Bio-Cult Europe (Invitrogen, Breda, the Netherlands). The cells are allowed to attach for at least 3 days. Thereafter, medium is changed and 4-hr incubations with or without a somatotropin release inhibiting factor (SRIF) analogs is provided and 10 nM GH-releasing hormone (GHRH) in 1 mL complete culture medium is initiated, using about four dishes for every treatment group. The results of each experiment are expressed as percentile change of hormone release compared with control untreated dishes. The concentration of rat GH and PRL is determined by means of a commercially available rat GH and PRL assay (Amersham, United Kingdom).

For expression of the somatostatin receptor subtype sst 2 and sst1,3,5 in rat colon carcinoma (CC531) cells and Chinese hamster ovaries (CHO)-K1 cells, respectively, human sst1, sst2, sst3 or sst5 cDNA in pBluescript (pBS) are excised from pBS and inserted into the Nhe-1/Sali cloning site of a retroviral expression vector pCi-neo. The selection is made by the geneticine resistance gene (G418). This vector is used to stably transfect (using DOTAP) CC531 and CHO-K1 cells. Stably transfected CC531 and CHO-K1 cells are selected and cultured in RPMI 1640 medium or nutrient mixture F12 (HAM) medium supplemented with penicillin (100 U/mL), streptomycin (100 μg/mL), fungizone (0.25 μg/mL) and 10% FCS+geneticine (0.5 mg/mL), respectively.

Competitive binding experiments are performed with membranes prepared from CC531 (sst2) and CHO-K1 (sst1, 3,5) cells expressing the respective human somatostatin receptor subtype (see, e.g., Reubi, Life Sci. 36(19):1829-36 1985). Membrane preparations (corresponding to about 25-50 μg protein) of cultured cells are incubated in a total volume of 100 μl at room temperature for 45 minutes with 40.000 cpm $^{125}$I-labeled [Tyr$^{111}$]-Somatostatin-14 (2000 Ci/mmol), in the presence of increasing amounts of unlabeled analogs. At the end of the incubation time, 1 ml ice-cold Hepes buffer (10 mM Hepes, 5 mM $MgCl_2$ and 0.02 g/liter bacitracin, pH 7.6) is added and membrane-bound radioactivity is separated from unbound by centrifugation during 2 min at 14,000 rpm in an Eppendorf microcentrifuge. The remaining pellet is washed in ice-cold Hepes buffer, and the final pellet is counted in a γ-counter. Specific binding is defined as the total amount of radioligand bound minus that bound in the presence of 1 M unlabeled analog.

For a further description of biological assays please see: Hofland and Lamberts, Front Horm Res. 32:235-52, 2004; Hofland et al., J Clin Endocrinol Metab. 89(4):1577-85, 2004; Ferone et al., Am J Physiol Endocrinol Metab. 283(5):E1056-66, 2002; and Hofland et al., Endocrinology. 136(9):3698-706, 1995).

Such experiments investigate the properties of RC-121 and use this information to improve the properties of potency and selectivity at the hsst2 and hsst5 receptors and resistance to enzymatic degradation. Such work has led to increased interest in the role of the residues at positions 1 and 8 for controlling receptor selectivity through interaction with extracellular loop III (ECLIII) located between transmembrane helices VI and VII.

Thus, a series of analogs of RC-121 were synthesized as described above and characterized as described herein. For example, the biological results for [D-Phe$^1$-Asp$^8$] (3), will demonstrate a selectivity for receptors hsst2 and hsst5.

Residue 8 of the analogs was maintained as Thr or Asp, both D- and L-isomers, and modified the D-Phe in position 1. Asp was chosen as a modification for residue 8. For modifications in position 1, the unnatural amino acid (4-aminomethyl)-phenylalanine, which has the characteristics of both hydrophobicity and basicity was prepared. It was believed that a weakly basic amino acid residue with an aromatic side chain in position 1, such as the amino acid building block (4-amino)-D-Phe-OH, may enhance the potencies of the analogs. Accordingly, residue 1, H-D-Phe-OH, was replaced with (4-amino)-D-Phe-OH in RC-121, D-Phe-c[Cys-Tyr-D-Trp-Lys-Val-Cys]-Thr-NH$_2$. The binding affinities and functional assay results for this group of target structures are assayed accordingly.

Compounds with (4-amino)-D-Phe-OH in position 1 were expected to exhibit potent and selective binding at receptors hsst2 and hsst5. Compound [(4-amino)-D-Phe$^1$-Thr$^8$](2) is expected to be selective at the hsst2 receptor by an order of magnitude compared to the hsst5 receptor. Such compounds can serve as inhibitor of GH and PRL release.

To study the binding affinities of the analogs, iodination assays can be performed. Radioiodination is a useful tool for the determination of tissue distribution of somatostatin receptors and for delivering toxic levels of radiation to somatostatin receptor-positive tumors, since several types of cancers express high densities of somatostatin receptors. Iodine has been extensively used for radiolabeling or chemical modification of peptides and proteins. Radioiodinated analogs of hormones are used in binding assays for displacement studies (competitive binding assays).

The peptides of the invention have two aromatic residues, Tyr and (4-amino)-D-Phe-OH. The next generation of modifications focused on iodination of the residues with aromatic side chains. Using monoiodinated building blocks 11 and 12, several iodinated peptidomimetics were synthesized and characterized.

Compound [(4-amino)-D-Phe$^3$-(3-iodo)Tyr$^3$-Thr$^8$] (6), was synthesized with an iodine on tyrosine, and [(4-amino-3-iodo)-D-Phe$^1$-Thr$^8$] (7) with an iodine on 4-amino-D-phenylalanine. In addition, the effect of adding two monoiodinated residues in the molecules can also be examined. Thus, compounds [(4-amino-3-iodo)-D-Phe$^1$-(3-iodo)Tyr$^3$-Thr$^8$] (9) and (4-amino-3-iodo)-D-Phe$^1$-(3-iodo)Tyr$^3$-Asp$^8$] (10), were prepared, the former with Thr in position 8, the latter with Asp in position 8. The activities of target molecules with or without iodine are compared and the activity related to their conformations.

Peptides [(4-amino-3-iodo)-D-Phe$^1$-Thr$^8$] (7) and [(4-amino-3-iodo)-D-Phe$^1$-(3-iodo)-Tyr$^3$-Thr$^8$] (9) are expected to exhibited potent and selective binding for hsst2 and 5 receptors, as well as increased ability to inhibit both GH and PRL.

The somatostatin analogs of the invention are selective for receptors hsst2 and hsst5, with inhibitory activity on GH and PRL comparable to that of somatostatin.

β-methylated analogs of Trp were synthesized enantioselectively and incorporated into the cyclic hexapeptide analog L-363, 301. The binding potencies and selectivities of c[Pro-Phe-(2R,3S)-β-MeTrp-Lys-Thr-Phe] and c[Pro-Phe-(2R,3R)-β-MeTrp-Lys-Thr-Phe] at somatostatin receptors hsst1-5 were determined, to further examine the results. In those studies, the (2R,3S) analog was more potent than the parent peptide, while the (2R,3R) analog was much less active. Both compounds bound to receptor hsst2 in nanomolar range. The analogs proved to be highly selective for hsst2, in contrast with the standard compound L-363, 301, which binds well to both receptors hsst2 and hsst5.

The peptide containing the (2R,3S)-β-MeTrp diastereomer possesses the "correct" combination of features that allow it to bind very well to hsst2. This finding has consequences for the future design of hsst2-selective somatostatin analogs.

Statistical analysis. The statistical significance of the difference between mean values was determined using one-way analysis of variance (ANOVA). When significant overall effects were obtained by this method, comparisons were made using Newman-Keuls multiple comparison test. Data are expressed as mean±sem. A P value less than 0.05 was considered significant. Calculation of the IC$_{50}$ values for displacement of $^{125}$I-labeled [Tyr$^{111}$]-Somatostatin-14 was performed using the GraphPad Prism (San Diego, Calif.) computerized program.

A number of embodiments of the invention have been described. Nevertheless, it will be understood that various modifications may be made without departing from the spirit and scope of the invention. Accordingly, other embodiments are within the scope of the following claims.

What is claimed is:

1. A method for reducing the release of growth hormone and/or thyroid stimulating hormone from the anterior pituitary of a subject, comprising administering an effective amount of a compound selected from any one of 4-amino-D-Phe-c[Cys-Tyr-D-Trp-Lys-Val-Cys]-Asp-NH$_2$ (SEQ ID NO:1); 4-amino-D-Phe-c[Cys-Tyr-D-Trp-Lys-Val-Cys]-Thr-NH$_2$; 4-amino-D-Phe-c[Cys-Tyr-D-Trp-Lys-Val-Cys]-D-Asp-NH$_2$; 4-amino-D-Phe-c[Cys-Tyr-D-Trp-Lys-Val-Cys]-D-Thr-NH$_2$; 4-amino-D-Phe-c[Cys-(3-iodo)-Tyr-D-Trp-Lys-Val-Cys]-Thr-NH$_2$; 4-amino-3-iodo-D-Phe-c[Cys-Tyr-D-Trp-Lys-Val-Cys]-Thr-NH$_2$; 4-amino-3-iodo-D-Phe-c[Cys-Tyr-D-Trp-Lys-Val-Cys]-Asp-NH$_2$; 4-amino-3-iodo-D-Phe-c[Cys-(3-iodo)-Tyr-D-Trp-Lys-Val-Cys]-Thr-NH$_2$; 4-amino-3-iodo-D-Phe-c[Cys-(3-iodo)-Tyr-D-Trp-Lys-Val-Cys]-Asp-NH$_2$; and D-Phe-c[Cys-Tyr-D-Trp-Lys-Val-Cys]-Asp-NH$_2$, or a pharmaceutically acceptable salt thereof.

2. The method of claim 1, wherein administering the compound reduces the subject's blood levels of growth hormone in comparison to the subject's growth hormone level prior to receiving the compound.

3. The method of claim 2, wherein the subject is a patient characterized by having elevated blood levels of growth hormone.

4. The method of claim 3, where the subject has acromegaly.

5. The method of claim 1, wherein administering the compound reduces the subject's blood levels of thyroid stimulating hormone (TSH) in comparison to the subject's TSH level prior to receiving the compound.

6. The method of claim 1, wherein the compound is administered intravenously or subcutaneously.

7. A method for reducing the release of insulin and/or glucagon from the pancreas of a subject, comprising administering an effective amount of a compound selected from any one of 4-amino-D-Phe-c[Cys-Tyr-D-Trp-Lys-Val-Cys]-Asp-NH$_2$ (SEQ ID NO:1); 4-amino-D-Phe-c[Cys-Tyr-D-Trp-Lys-Val-Cys]-Thr-NH$_2$; 4-amino-D-Phe-c[Cys-Tyr-D-Trp-Lys-Val-Cys]-D-Asp-NH$_2$; 4-amino-D-Phe-c[Cys-Tyr-D-Trp-Lys-Val-Cys]-D-Thr-NH$_2$; 4-amino-D-Phe-c[Cys-(3-iodo)-Tyr-D-Trp-Lys-Val-Cys]-Thr-NH$_2$; 4-amino-3-iodo-D-Phe-c[Cys-Tyr-D-Trp-Lys-Val-Cys]-Thr-NH$_2$; 4-amino-3-iodo-D-Phe-c[Cys-Tyr-D-Trp-Lys-Val-Cys]-Asp-NH$_2$; 4-amino-3-iodo-D-Phe-c[Cys-(3-iodo)-Tyr-D-Trp-Lys-Val-Cys]-Thr-NH$_2$; 4-amino-3-iodo-D-Phe-c[Cys-(3-iodo)-Tyr-D-Trp-Lys-Val-Cys]-Asp-NH$_2$; and D-Phe-c[Cys-Tyr-D-Trp-Lys-Val-Cys]-Asp-NH$_2$, or a pharmaceutically acceptable salt thereof.

8. The method of claim 7, wherein administering the compound results in an increase in the subject's blood glucose levels in comparison to the subject's glucose level prior to receiving the compound.

9. The method of claim 7, wherein the subject is a patient characterized by having hypoglycemia.

10. The method of claim 9, wherein the subject has hypoglycemia from insulin treatment for diabetes mellitus.

11. The method of claim 7, wherein the compound is administered intravenously or subcutaneously.

12. A method for reducing the activity and growth of a tumor in a subject, comprising administering an effective amount of a compound selected from any one of 4-amino-D-Phe-c[Cys-Tyr-D-Trp-Lys-Val-Cys]-Asp-NH$_2$ (SEQ ID NO:1); 4-amino-D-Phe-c[Cys-Tyr-D-Trp-Lys-Val-Cys]-Thr-NH$_2$; 4-amino-D-Phe-c[Cys-Tyr-D-Trp-Lys-Val-Cys]-D-Asp-NH$_2$; 4-amino-D-Phe-c[Cys-Tyr-D-Trp-Lys-Val-Cys]-D-Thr-NH$_2$; 4-amino-D-Phe-c[Cys-(3-iodo)-Tyr-D-Trp-Lys-Val-Cys]-Thr-NH$_2$; 4-amino-3-iodo-D-Phe-c[Cys-Tyr-D-Trp-Lys-Val-Cys]-Thr-NH$_2$; 4-amino-3-iodo-D-Phe-c[Cys-Tyr-D-Trp-Lys-Val-Cys]-Asp-NH$_2$; 4-amino-3-iodo-D-Phe-c[Cys-(3-iodo)-Tyr-D-Trp-Lys-Val-Cys]-Thr-NH$_2$; 4-amino-3-iodo-D-Phe-c[Cys-(3-iodo)-Tyr-D-Trp-Lys-Val-Cys]-Asp-NH$_2$; and D-Phe-c[Cys-Tyr-D-Trp-Lys-Val-Cys]-Asp-NH$_2$, or a pharmaceutically acceptable salt thereof.

13. The method of claim 12, wherein administering the compound results in a decrease in the secretory activity of the tumor in comparison to the secretory activity prior to administering the compound.

14. The method of claim 12, wherein the tumor is a growth hormone-producing adenoma, TSH-producing adenoma, endocrine inactive adenoma, carcinoid, islet-cell carcinoma, a pancreatic hormone secreting tumor, or a gastrointestinal secreting tumor.

15. The method of claim 14, wherein the tumor is a carcinoid.

16. The method of claim 12, wherein the compound is administered intravenously or subcutaneously.

* * * * *